United States Patent
Muse et al.

(10) Patent No.: US 11,751,774 B2
(45) Date of Patent: Sep. 12, 2023

(54) ELECTRONIC AUSCULTATION AND IMPROVED IDENTIFICATION OF AUSCULTATION AUDIO SAMPLES

(71) Applicant: UnitedHealth Group Incorporated, Minnetonka, MN (US)

(72) Inventors: Jon Kevin Muse, Thompsons Station, TN (US); Gregory J. Boss, Saginaw, MI (US); Rama S. Ravindranathan, Edison, NJ (US); Marilyn L. Gordon, Cherry Hill, NJ (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 195 days.

(21) Appl. No.: 17/096,035

(22) Filed: Nov. 12, 2020

(65) Prior Publication Data

US 2022/0142490 A1     May 12, 2022

(51) Int. Cl.
*A61B 5/0255*      (2006.01)
*G10L 25/66*      (2013.01)
*A61B 5/0205*      (2006.01)
*G06V 40/10*      (2022.01)

(52) U.S. Cl.
CPC .......... *A61B 5/0255* (2013.01); *A61B 5/0205* (2013.01); *G06V 40/10* (2022.01); *G10L 25/66* (2013.01); *G06V 40/15* (2022.01)

(58) Field of Classification Search
CPC ...... A61B 5/0255; A61B 5/0205; G10L 25/66
See application file for complete search history.

(56) References Cited

U.S. PATENT DOCUMENTS

| 6,168,568 B1 | 1/2001 | Gavriely |
| 7,753,856 B2 | 7/2010 | Dziubinski |
| 8,506,480 B2 | 8/2013 | Banet et al. |

(Continued)

FOREIGN PATENT DOCUMENTS

WO    WO-2019229543 A1 * 12/2019 ............... A61B 5/08

OTHER PUBLICATIONS

Abnousi, Freddy et al. "A Novel Noninvasive Method for Remote Heart Failure Monitoring: the EuleriAn video Magnification apPLications in heart Failure studY (AMPLIFY)," npj Digital Medicine, Aug. 21, 2019, vol. 2, No. 1, pp. 1-6. DOI: 10.1038/S41746-019-0159-0.

(Continued)

*Primary Examiner* — Tammie K Marlen
(74) *Attorney, Agent, or Firm* — ALSTON & BIRD LLP

(57) ABSTRACT

Embodiments of the invention provide methods for identifying suspect heart or lung sounds and methods for generating an isolated sound sample. In some embodiments, a method for identifying suspect heart or lung sounds comprises obtaining, by processing circuitry, an instance of data samples comprising at least two audio samples and respiratory and/or cardiac cycle data, the audio samples comprising auscultation sounds of an individual, based on the respiratory and/or cardiac cycle data, processing the at least two audio samples to generate a plurality of sound samples, identifying a primary sound sample, generating at least one of a modified secondary sound or a modified baseline sample and combining the modified secondary sound sample or the modified baseline sample with the primary sound sample to generate an isolated sound sample.

20 Claims, 8 Drawing Sheets

(56) References Cited

U.S. PATENT DOCUMENTS

| | | |
|---|---|---|
| 9,125,564 B2 | 9/2015 | Schmidt et al. |
| 9,521,956 B2 | 12/2016 | Bedingham et al. |
| 9,750,429 B1 | 9/2017 | Sackner et al. |
| 10,004,473 B2 | 6/2018 | Tsai et al. |
| 10,055,549 B2 | 8/2018 | Chung et al. |
| 10,080,528 B2 | 9/2018 | DeBusschere et al. |
| 10,182,727 B2 | 1/2019 | Gargiulo et al. |
| 10,217,218 B2 | 2/2019 | Wu et al. |
| 10,398,364 B2 | 9/2019 | Cheng |
| 10,595,813 B2 | 3/2020 | Song et al. |
| 10,702,166 B1 | 7/2020 | Freeman et al. |
| 10,709,414 B1 | 7/2020 | McLane |
| 2007/0055151 A1 | 3/2007 | Shertukde et al. |
| 2016/0036965 A1 | 2/2016 | Kim |
| 2016/0086161 A1 | 3/2016 | Zhou et al. |
| 2016/0209636 A1 | 7/2016 | Baleine et al. |
| 2017/0172459 A1* | 6/2017 | Bernstein ............. A61B 5/6823 |
| 2017/0209115 A1 | 7/2017 | Lonnroth et al. |
| 2017/0325779 A1 | 11/2017 | Spina et al. |
| 2018/0108440 A1 | 4/2018 | Stevens et al. |
| 2018/0301221 A1 | 10/2018 | Rothman |
| 2018/0325407 A1 | 11/2018 | Varadan et al. |
| 2019/0014408 A1 | 1/2019 | Tang |
| 2019/0083038 A1 | 3/2019 | Griffin et al. |
| 2019/0142686 A1 | 5/2019 | Lee |
| 2019/0192110 A1 | 6/2019 | Parvaneh et al. |
| 2019/0216350 A1 | 7/2019 | Sullivan et al. |
| 2019/0282178 A1 | 9/2019 | Volosin et al. |
| 2019/0298269 A1 | 10/2019 | Atashbar et al. |
| 2020/0008684 A1 | 1/2020 | Feinberg |
| 2020/0060641 A1* | 2/2020 | Shekhar ............. A61B 5/14542 |
| 2020/0111578 A1 | 4/2020 | Koblick et al. |
| 2021/0287004 A1 | 9/2021 | Wexler et al. |
| 2021/0337307 A1 | 10/2021 | Wexler et al. |
| 2022/0196678 A1 | 6/2022 | Wilson et al. |

OTHER PUBLICATIONS

Gnitecki, January et al. "Separating Heart Sounds From Lung Sounds—Accurate Diagnosis of Respiratory Disease Depends on Understanding Noises," In IEEE Engineering in Medicine and Biology Magazine, Jan./Feb. 2007, pp. 20-29. DOI: 10.1109/MEMB.2007.289118.

Li, Shih-Hong et al. "Design of Wearable Breathing Sound Monitoring System for Real-Time Wheeze Detection," Sensor, (2017), vol. 17, No. 1, pp. 1-15. DOI: 10.3390/s17010171.

Marani, Roberto et al. "High Quality Heart and Lung Auscultation System for Diagnostic Use on Remote Patients in Real Time," The Open Biomedical Engineering Journal, (2010), vol. 4, pp. 250-256.

Michler, Fabian et al. "A Clinically Evaluated Interferometric Continuous-Wave Radar System for the Contactless Measurement of Human Vital Parameters," Sensors, (2019), vol. 11, No. 2492, pp. 1-19. DOI: 10.3390/s19112492.

Pramono, Renard Xaviero Adhi et al. "Automatic Adventitious Respiratory Sound Analysis: A Systematic Review," PLos|ONE, vol. 12, No. 5:e0177296, May 26, 2017, pp. 1-43. DOI: 10.1371/journal.pone.0177926.

Notice of Allowance for U.S. Appl. No. 17/095,853, dated Aug. 16, 2022, (15 pages). United States Patent and Trademark Office, US.

NonFinal Office Action for U.S. Appl. No. 18/060,635, dated Mar. 24, 2023, (7 pages), United States Patent and Trademark Office, US.

\* cited by examiner

ELECTRONIC AUSCULTATION AND IMPROVED IDENTIFICATION OF AUSCULTATION AUDIO SAMPLES

BACKGROUND

Auscultation is the listening to the internal sounds of the body for the purposes of, for example, examining the circulatory and/or respiratory systems. As auscultation often depends on the medically trained ear of a physician, using auscultation to perform regular monitoring of patients, especially patients who are at home or otherwise not in a clinical setting, is generally not attempted.

BRIEF SUMMARY

In general, embodiments of the present invention provide methods, apparatus, systems, computing entities, and/or the like for performing electronic auscultation and processing captured auscultation data samples to determine whether any suspect heart or lung sounds are present. In various embodiments, the captured auscultation data samples are processed to identify any suspect heart or lung sounds present in the captured auscultation data samples. In various embodiments, the identified suspect heart or lung sounds may be used to generate an automated diagnosis and/or provided through a dashboard, for example, for physician review.

In various embodiments, sensors may be placed on a patient's body. For example, the sensors may include audio sensors configured to record and/or digitize sound, pulse and/or heart rate sensors configured to detect a patient's pulse, stretch sensors configured to monitor the expansion and contraction of a patient's chest as the patient inhales and exhales, and/or the like. In an example embodiment, the sensors may be incorporated into and attached to a wearable device, such as a vest and/or the like to enable easy, reproducible, and accurate placement of the sensors on the patient's body (e.g., chest, back, and/or the like). The sensors may then be used to capture one or more instances of data samples. The data samples may include information/data indicative of a patient's heart rate (e.g., pulse and/or the like) and audio samples of heart and/or lung sounds of the patient. The audio samples may be processed to generate heart sound samples and/or lung sound samples (e.g., by removing the lung sounds from an audio sample to generate a heart sound sample or by removing the heart sounds form an audio sample to generate a lung sound sample). By mixing and/or combining different audio samples that were captured simultaneously by different audio sensors on the patient's body in an out of phase manner, any suspect sounds present may be isolated and analyzed. For example, any suspect sounds present in the audio samples may be identified and/or classified.

In various embodiments, when a suspect sound is identified in an audio sample, additional instances of data samples may be captured. For example, instructions may be provided to a patient to say a particular word, breathe or move their body in a particular manner, assume a particular body position, and/or the like. For example, the instructions may be configured to enable improved detection and/or determination of details regarding the suspect sound. The additional instances of data samples may be analyzed to isolate any suspect sounds present therein. The suspect sounds may then be stored (e.g., in a memory, database, electronic health record, and/or the like) and/or provided for physician review.

In accordance with an aspect of the present disclosure, a method for identifying suspect heart or lung sounds is provided, the method comprising: obtaining, by processing circuitry, an instance of data samples, the instance of data samples comprising at least two audio samples and respiratory and/or cardiac cycle data, the audio samples comprising auscultation sounds of an individual; based on the respiratory and/or cardiac cycle data, processing the at least two audio samples to generate (a) at least two lung sound samples or (b) at least two heart sound samples; identifying a primary sound sample and at least one secondary sound sample from the (a) at least two lung sound samples or (b) at least two heart sound samples; generating at least one of (a) a modified secondary sound sample by changing a phase of the at least one secondary sound sample by 180 degrees or (b) a modified baseline sample by changing a phase of a baselines sample accessed from memory by 180 degrees; combining the at least one of (a) the modified secondary sound sample or (b) the modified baseline sample with the primary sound sample to generate an isolated sound sample; and determining whether the isolated sound sample includes a suspect sound.

In accordance with another aspect of the present disclosure, a method for generating an isolated sound sample is provided, the method comprising: identifying, by a processing element, a suspect sound present in an auscultation audio sample captured by one or more sensors on a patient; identifying, by the processing element, one or more contexts for capturing additional instances of data samples based on the suspect sound; causing, by the processing element, an output device to provide instructions regarding the one or more contexts; obtaining, by the processing element, one or more additional instances of data samples, each of the one or more additional instances of data samples captured while the patient was performing one of the one or more contexts; analyzing, by the processing elements at least one of the one or more additional instances of data samples to generate an isolated sound sample, the analyzing of the one or more additional instances of data samples comprising: identifying a primary sound sample and at least one secondary sound sample from auscultation audio samples of the at least one of the one or more additional instances of data samples; generating a modified secondary sound sample or a modified baseline sample by changing the phase of the at last one secondary sound sample or a baseline sample by 180 degrees; and combining the modified secondary sound sample or the modified baseline sample with the primary sound sample to generate an isolated sound sample.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 2:
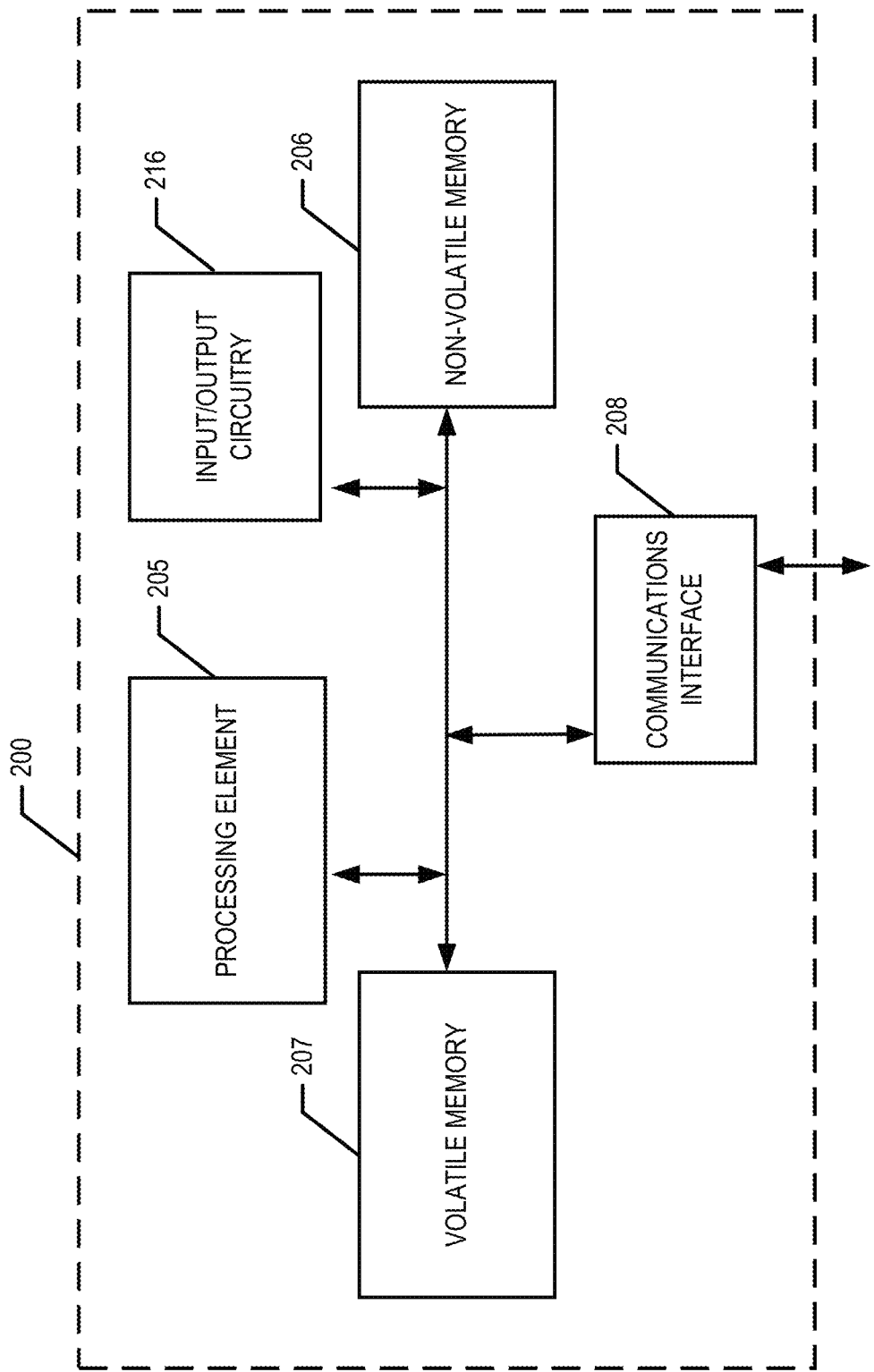
FIG. 2 illustrates an example network computing entity in accordance with some embodiments discussed herein.
Figure 3:
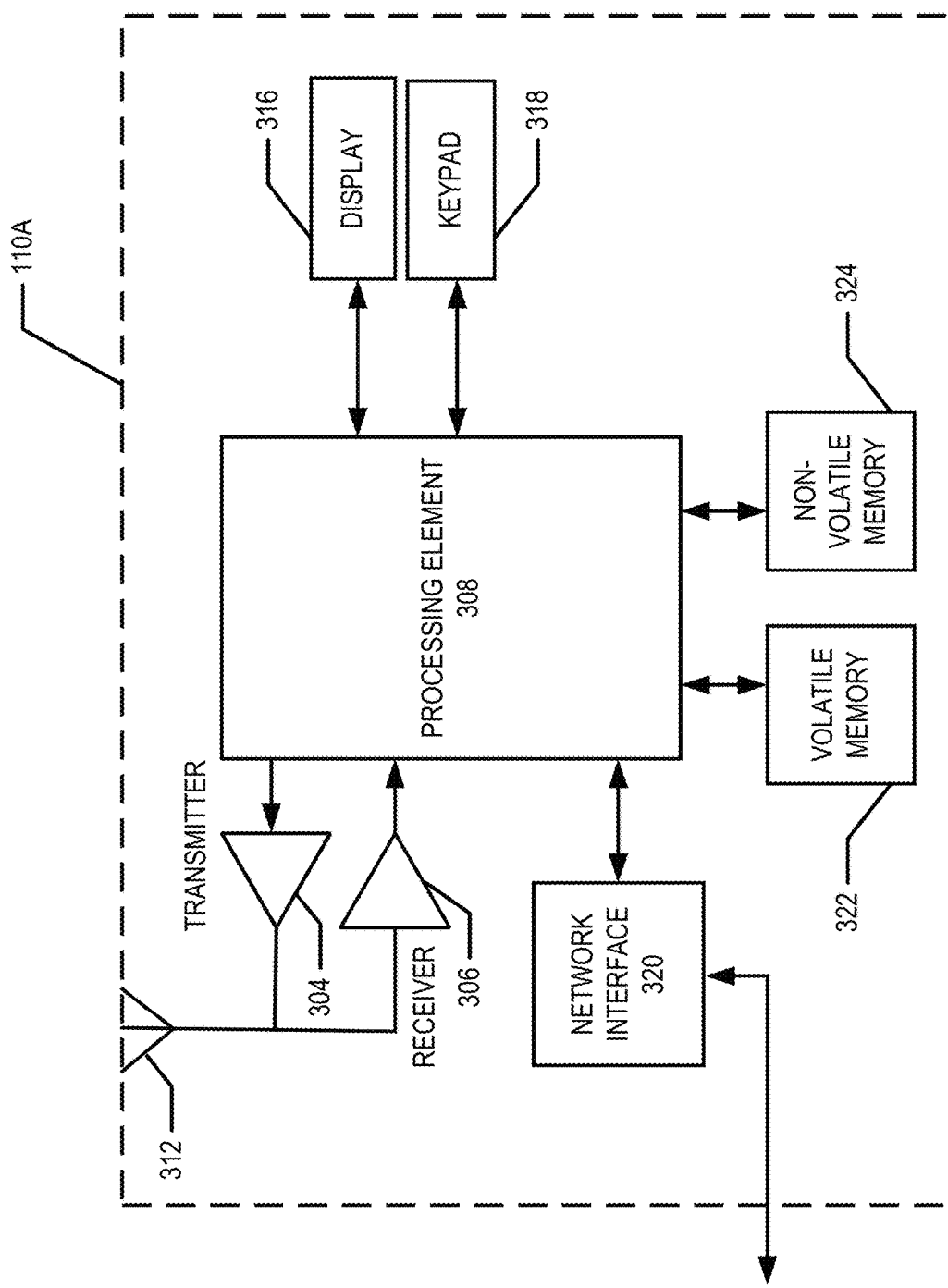
FIG. 3 illustrates an example user computing entity in accordance with some embodiments discussed herein.
Figure 4:
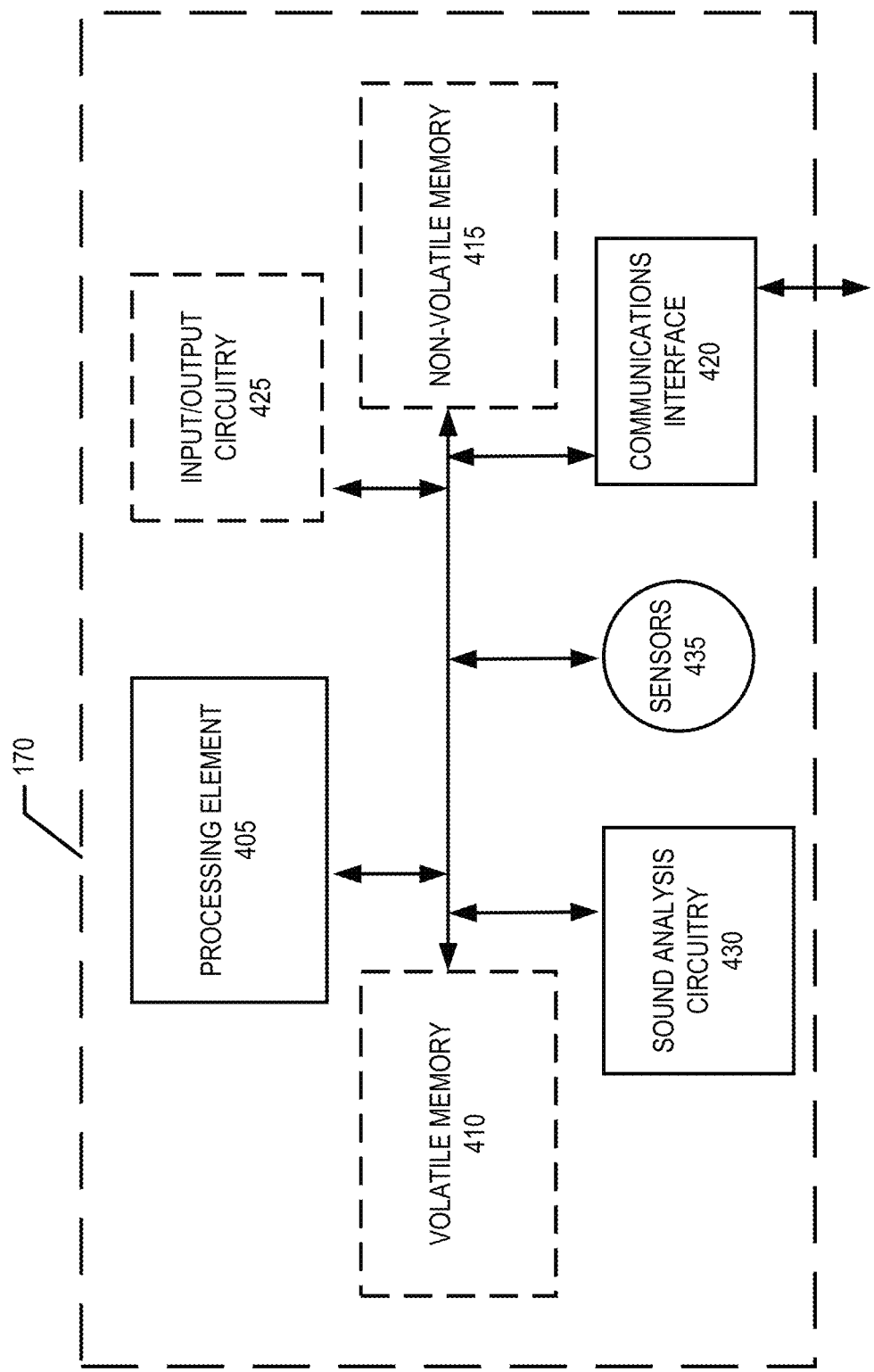
FIG. 4 illustrates an example monitoring device in accordance with some embodiments discussed herein.
Figure 5:
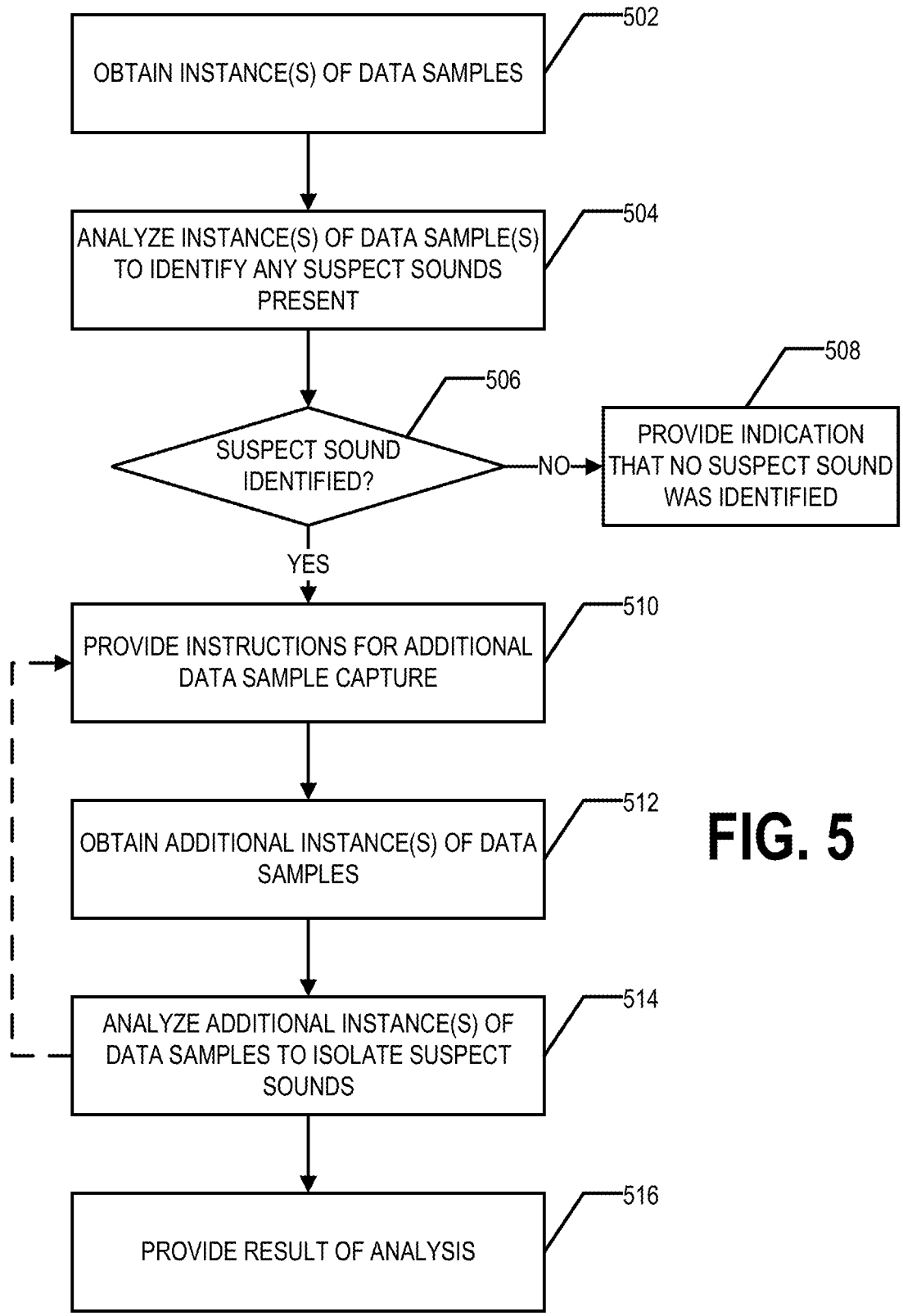
Figure 6:
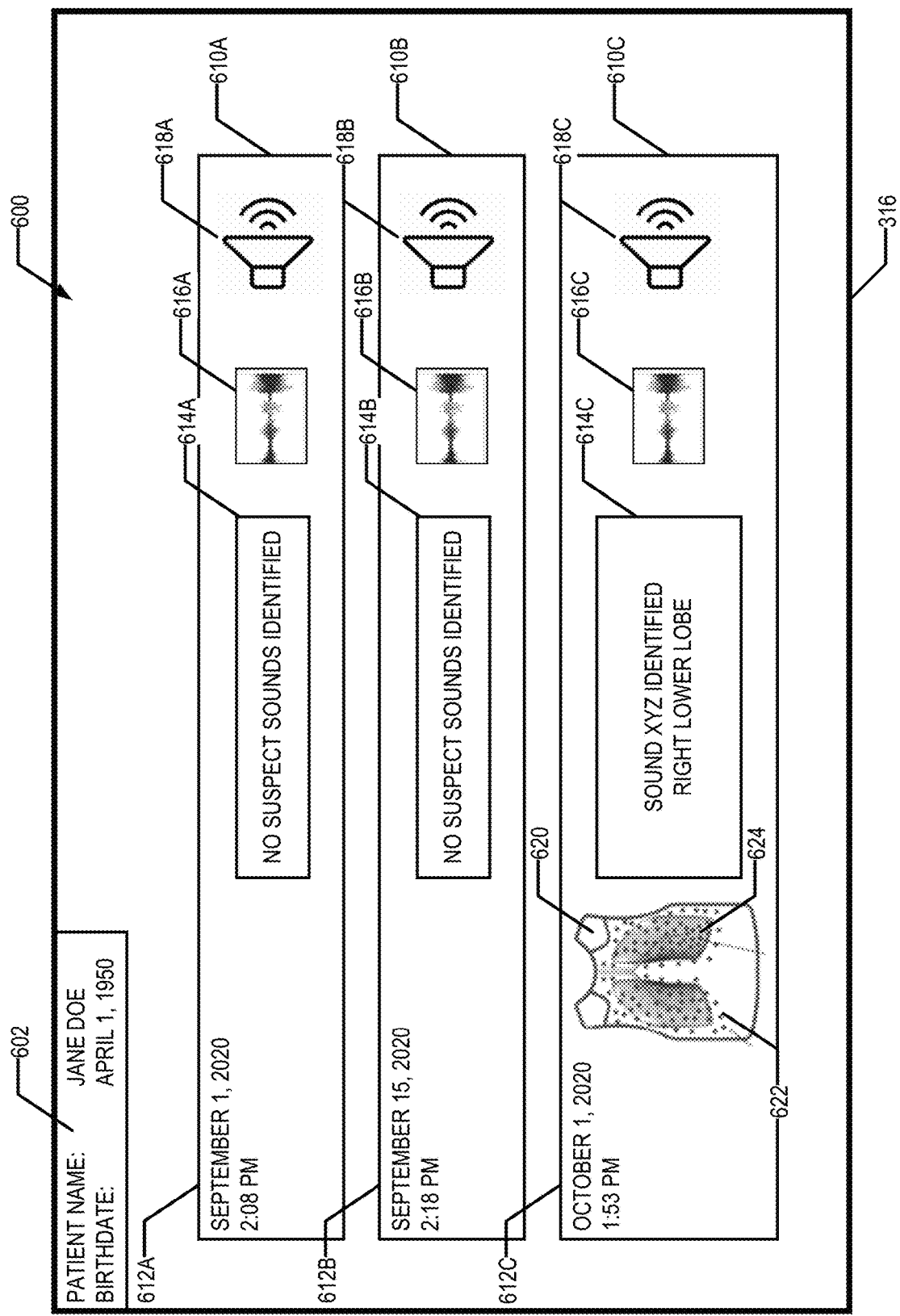
Figure 7:
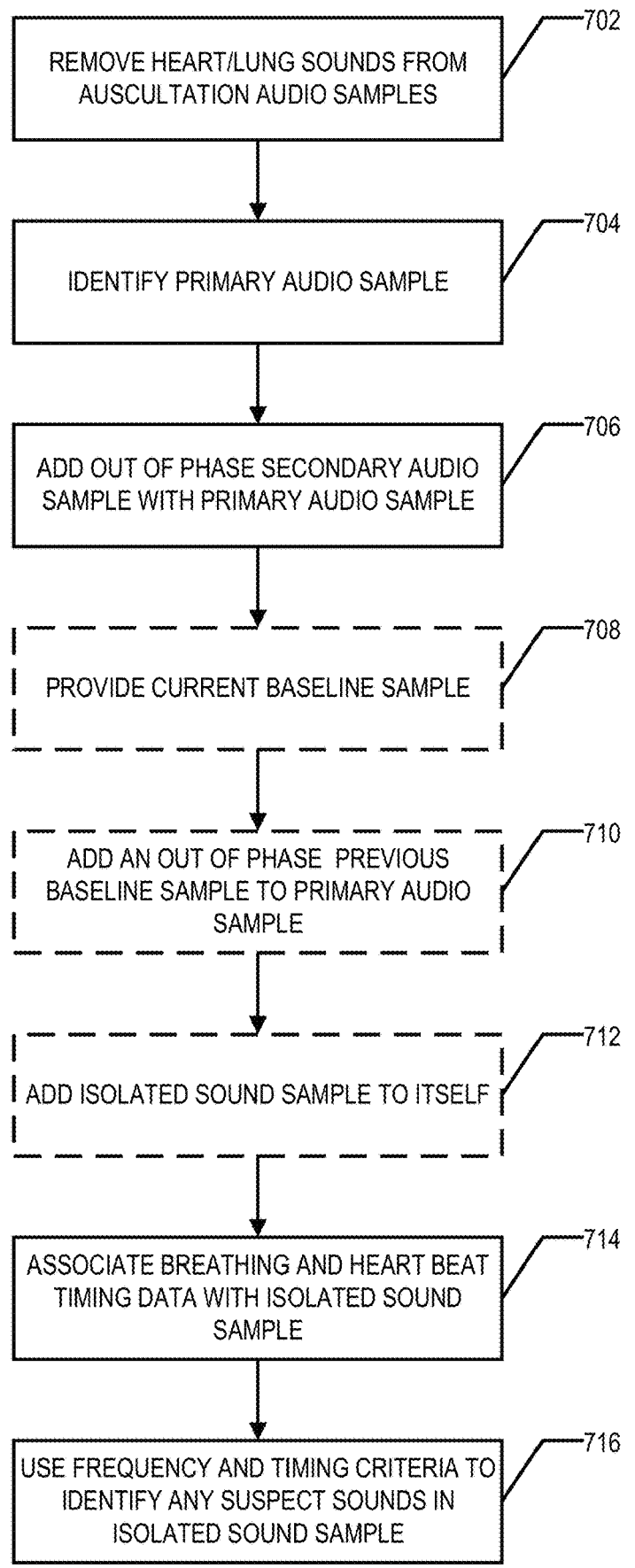
Figure 8:
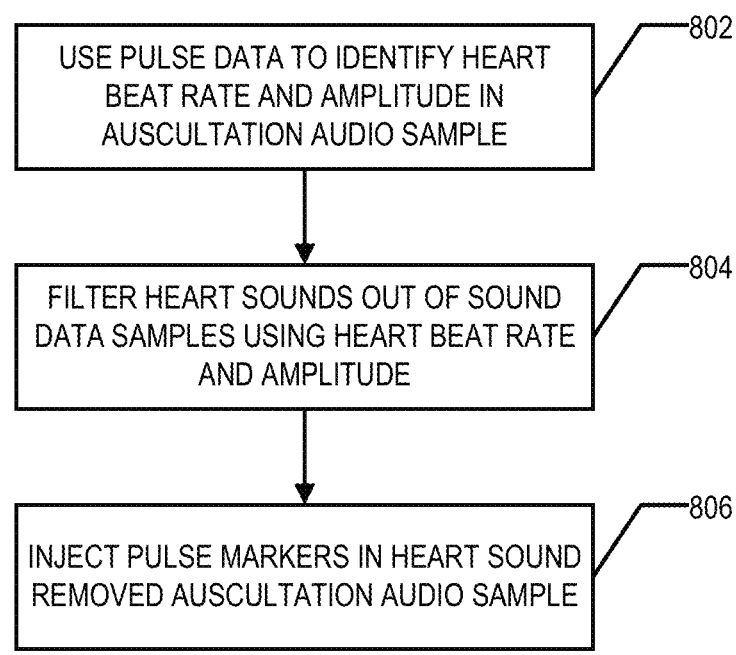

FIG. 5 provides a flowchart illustrating process, procedures, operations, and/or the like performed, for example, by a monitoring device of FIG. 4, user computing entity of FIG. 3, or network computing entity of FIG. 2, to identify any suspect sounds present in auscultation audio samples corresponding to functioning of a patient's heart and/or lungs, in accordance with various embodiments discussed herein;

FIG. 6 provides an example screen view of a monitoring dashboard, in accordance with an example embodiment;

FIG. 7 provides a flowchart illustrating process, procedures, operations, and/or the like performed, for example, by a monitoring device of FIG. 4, user computing entity of FIG. 3, or network computing entity of FIG. 2, to analyze an instance of data samples to identify any suspects sounds present therein, in accordance with various embodiments discussed herein; and FIG. 8 provides a flowchart illustrating process, procedures, operations, and/or the like performed, for example, by a monitoring device of FIG. 4, user computing entity of FIG. 3, or network computing entity of FIG. 2, to remove heart sounds from an auscultation audio sample, in accordance with various embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. Overview

Various embodiments provide methods, apparatus, systems, computer program products, and/or the like for performing electronic auscultation; determining whether suspect sounds are present in auscultation audio samples; guiding a user through capture of additional instances of data samples (e.g., auscultation audio samples) and performing processing and/or analysis thereof; providing information, audio samples, and/or graphical representations of captured auscultation audio samples, and/or suspect sounds identified in therein (e.g., via a dashboard and/or the like). For example, a monitoring device 170 may be used to capture one or more instances of data samples. In various embodiments, an instance of data samples comprises data samples that were captured simultaneously (e.g., during the same data sample capture session). In an example embodiment, an instance of data samples comprises one or more auscultation audio samples corresponding to a patient and may include one or more data signals used for tracking the patient's cardiac and/or respiratory cycle. For example, a monitoring device 170 comprising a plurality of sensors 435 may be used to capture auscultation audio samples from a patient. The sensors 435 of the monitoring device 435 may be used to capture data signals for tracking the patient's cardiac and/or respiratory cycle. As just one example, a monitoring device 170 may be embodied as a wearable device having sensors 435 incorporated therein. The wearable device may be embodied as a vest, a shirt, pants, underwear, socks, a hat, and/or the like. As a specific example, a vest having sensors 435 incorporated therein may be utilized to generate sound data indicative of sounds of a wearing patient's heart and/or lungs.

The monitoring device 170 and/or other computing entity (e.g., user computing entity 110 and/or network computing entity 130) may be configured to process and/or analyze the auscultation audio samples and/or data signals for tracking the patient's cardiac and/or respiratory cycle. In an example embodiment, processing the auscultation audio samples includes modifying the phase of at least one auscultation audio sample (and/or a voltage signal representing the at least one auscultation audio sample) and combining the at least one auscultation audio signal (and/or a voltage signal representing the at least one auscultation audio sample) with another one of the auscultation audio samples (and/or a voltage signal representative thereof). For example, such combination of auscultation audio samples may be used to remove background noise from the samples such that any suspect sounds present in the auscultation audio samples is isolated for further analysis. The resultant audio sample (and/or voltage signal representative thereof) may be analyzed and/or the like to determine whether any suspect sounds are present therein and/or to identify any suspect sounds present therein. In various embodiments, the suspect sounds may be indicative and/or symptoms of particular health conditions being present in the patient, particular health conditions that are present in the patient progressing and/or changing presentation, a state of a particular health condition that is present in the patient, and/or the like.

When suspect sounds are determined to be present and/or identified in the auscultation audio samples, additional instances of data samples may be captured. For example, the monitoring device 170 and/or a user computing entity 110 may provide instructions regarding a particular word a patient should speak, a particular manner in which a patient should breath or move their body, a particular body position a patient should assume, and/or the like while additional instances of data samples are being captured. For example, the particular word, breathing and/or movement, and/or body position may be selected as a particular word, breathing and/or movement, and/or body position that may highlight and/or provide diagnostic information regarding a suspect sound determined and/or identified to be present in an auscultation audio sample. The additional instances of data samples may be processed and/or analyzed to determine and/or identify any suspect sounds present therein. Information/data, audio samples, and/or graphical representations of the suspect sounds and/or corresponding to one or more instances of data samples may be stored (possibly in association with corresponding metadata) and/or provided for review by a user (e.g., the patient, a physician and/or other healthcare worker, and/or the like). In an example embodiment, a remote physician and/or other healthcare worker may determine a diagnosis and/or a treatment plan for a patient based on the information/data, audio samples, and/or graphical representations of the suspect sounds and/or corresponding to one or more instances of data samples. Thus, various embodiments enable the monitoring of patient heart and/or lung functioning, through the monitoring of auscultation audio samples, without requiring a physician or other healthcare worker trained in auscultation.

A. Technical Problem

Scientific medical study has proven that auscultation of a patient's chest and/or back are an important step in diagnosing long term and/or acute heart and/or lung issues. Certain sounds that may be present in the observed auscultation audio samples can be narrowed down to specific disorders and/or emergency conditions. Auscultation is generally performed by a physician or other trained healthcare worker, which limits the availability of auscultation as an at will technique for monitoring patients. While recording auscultation audio samples and analyzing these recordings in an automated manner have been attempted, these techniques tend to fail to provide an appropriate removal of heart sounds from lung sound samples and/or removal of lung sounds from heart sound samples.

B. Technical Solution

To solve the foregoing technical problems, an exemplary embodiment of the present invention provides auscultation audio sample processing that provides an isolated suspect sound sample that may be used for effective and efficient identification of suspect sounds of a patient's heart and/or lungs through auscultation-based monitoring of the patient's heart and/or lung functions. For example, by capturing multiple auscultation audio samples at different locations on the patient's chest and/or back simultaneously (e.g., by a plurality of sensors positioned within a sensor array on a patient's chest and/or back, such as sensors incorporated into a chest region and/or a back region of a vest) and then combining various ones of the auscultation audio samples in phase and/or out of phase (e.g., 180 degrees out of phase), isolated suspect sound samples may be generated. By isolating suspect sounds in the auscultation audio samples, the suspect sounds may be more effectively explored, studied, monitored, and/or the like. Additionally, the simultaneous capture of information for tracking the patient's cardiac and/or respiratory cycle enable simple removal of heart and/or lung sounds from an auscultation sample without adding artificial artifacts within the resultant sample. Moreover, various embodiments guide a patient through the capture of additional instances of data samples that provide additional information and/or context to a reviewing physician and/or other healthcare worker which enables physician attention to be directed to cases where a patient may need emergency assistance rather than routine monitoring. Furthermore, various embodiments enable the detection of suspect sounds generated by the functioning of the patient's lungs or heart that are not detectable by the human ear during physician performed auscultation. Thus, various embodiments provide for improved detection of suspect sounds in auscultation audio samples that may lead to improved or earlier treatment of issues with the functioning of the patient's heart or lungs.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing entities, computing entities, and/or the like. As such, embodiments of the present invention may take the form of an apparatus, system, computing entity, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing entities, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

Figure 1:
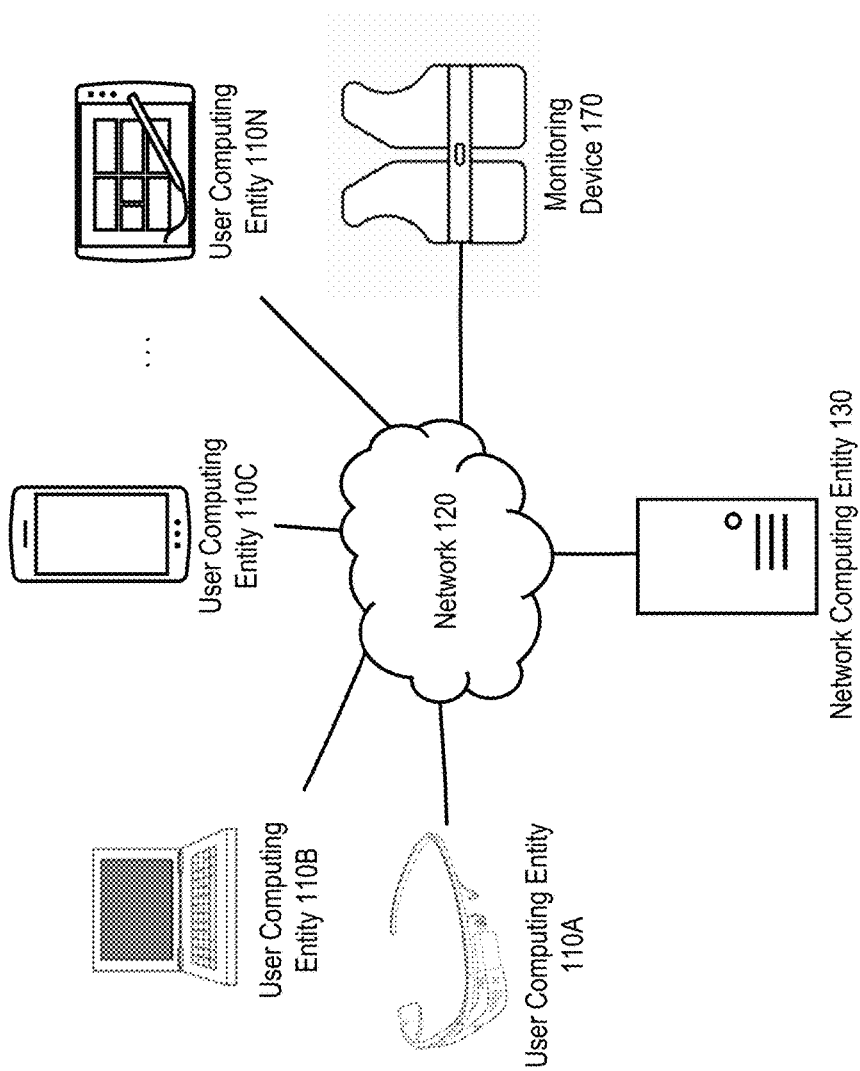
FIG. 1 is an exemplary overview of a system that can be used to practice embodiments of the present invention.

FIG. 1 provides an illustration of an exemplary embodiment of the present invention. FIG. 1 shows system 100 including an example network architecture for a system, which may include one or more devices and sub-systems that are configured to implement some embodiments discussed herein. As shown in FIG. 1, the system 100 may comprise a network computing entity 130, one or more user computing entities 110A-110N, one or more monitoring devices 170, one or more networks 120, and/or the like. Each of the components of the system may be in electronic communication with, for example, one another over the same or different wireless and/or wired networks 120 as discussed herein.

In various embodiments, the network computing entity 130, one or more user computing entities 110A-110N, one or more monitoring devices 170, and/or other computing entities may communicate with one another via network 120. In this regard, network 120 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, network 120 may include a cellular telephone, an 802.11, 802.16, 802.20, and/or WiMax network. Further, the network 120 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the group-based communication interface. In some embodiments, the protocol is a custom protocol of JSON objects sent via a Websocket channel. In some embodiments, the protocol is JSON over RPC, JSON over REST/HTTP, and the like.

User computing entities 110A-110N, monitoring device 170, and/or network computing entity 130 may each be implemented as one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, items/devices, vehicles, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. The depiction in FIG. 1 of "N" user computing entities is merely for illustration purposes. Any number of users and/or user computing entities 110 may be included in the system for accessing and/or implementing aspects of various embodiments discussed herein (e.g., via one or more interfaces). In one embodiment, the user computing entities 110A-110N may be configured to display or provide a monitoring dashboard on a display of the user computing entity for viewing; provide instructions for patient movement, body positioning, and/or speaking during the capturing of additional instances of data samples via a display or speaker of the user computing entity; and/or the like, which may be provided or pushed by the network computing entity 130 (and/or may be stored locally at one or more user computing entities 110A-110N and/or monitoring devices 170).

As indicated above, the user computing entities 110A-110N may be any computing entity as defined above. Electronic data received by the network computing entity 130 and/or monitoring device 170 by the user computing entities 110A-110N may be provided in various forms and via various methods. For example, the user computing entities 110A-110N may include desktop computers, laptop computers, smartphones, netbooks, tablet computers, wearables, and the like. In embodiments where a user computing entity 110A-110N is a mobile device, such as a smart phone or tablet, the user computing entity 110A-110N may execute an "app" such as a monitoring application to interact with the monitoring device 170. Such apps are typically designed to execute on mobile devices, such as tablets or smartphones. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with processing circuitry of a monitoring device 170, wired and wireless network interfaces, and other applications. Communication with hardware and software modules executing outside of the app is typically provided via application programming interfaces (APIs) provided by the mobile device operating system.

Additionally or alternatively, the user computing entity 110A-110N may interact with the network computing entity 130 and/or monitoring device 170 via a web browser. As yet another example, the user computing entity 110A-110N may include various hardware or firmware designed to interface with the network computing entity 130 and/or monitoring device 170. For example, a user computing entity 110A-110N may be in wired and/or wireless communication with a monitoring device 170 such that the monitoring device may be used to capture instances of data samples and/or process instances of data samples.

A. Exemplary Circuitry of a Network Computing Entity

FIG. 2 provides a schematic of circuitry 200, some or all of which may be included in, for example, network computing entity 130 and/or user computing entities 110A-110N. Any of the aforementioned systems or devices may include the circuitry 200 and may be configured to, either independently or jointly with other devices in a network 120 perform the functions of the circuitry 200 described herein. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As illustrated in FIG. 2, in accordance with some example embodiments, circuitry 200 can includes various means, such as processing element 205, volatile memory 207, non-volatile memory 206, communications interface 208, and/or input/output circuitry 216. As referred to herein, "circuitry" includes hardware, software and/or firmware configured to perform one or more particular functions. In this regard, the means of circuitry 200 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., non-volatile memory 206) that is executable by a suitably configured processing device (e.g., processing element 205), or some combination thereof.

Input/output circuitry 216 may be in communication with processing element 205 to receive an indication of a user input and/or to provide an audible, visual, mechanical, or other output to a user (e.g., provider and/or consumer). As such, input/output circuitry 216 may include support, for example, for a keyboard, a mouse, a joystick, a display, a touch screen display, a microphone, a speaker, a RFID reader, barcode reader, biometric scanner, and/or other input/output mechanisms. In embodiments wherein circuitry 200 is embodied as a server or database, aspects of input/output circuitry 216 may be reduced as compared to embodiments where circuitry 200 is implemented as an end-user machine (e.g., user computing entity 110) or other type of device designed for complex user interactions. In some embodiments (like other components discussed herein), input/output circuitry 216 may even be eliminated from circuitry 200. Alternatively, such as in embodiments wherein circuitry 200 is embodied as a server or database, at least some aspects of input/output circuitry 216 may be embodied on an apparatus used by a user that is in communication with circuitry 200. Input/output circuitry 216 may be in communication with the volatile memory 207, non-volatile memory 206, communications interface 208, and/or any other component(s), such as via a bus. One or more than one input/output circuitry and/or other component can be included in circuitry 200.

As indicated, in one embodiment, circuitry 200 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the circuitry 200 may communicate with other computing entities, one or more user computing entities 110A-110N, and/or the like.

As shown in FIG. 2, in one embodiment, the circuitry 200 may include or be in communication with one or more processing elements 205 (also referred to as processors, processing circuitry, and/or similar terms used herein interchangeably) that communicate with other elements within the circuitry 200 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the circuitry 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Non-volatile memory 206 may also be embodied as a data storage device or devices, as a separate database server or servers, or as a combination of data storage devices and separate database servers. Further, in some embodiments, non-volatile memory 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the relevancy prediction system may be stored. As a person of ordinary skill in the art would recognize, the information/data required for the operation of the relevancy prediction system may also be partially stored in the cloud data storage system and partially stored in a locally maintained data storage system.

Non-volatile memory 206 may include information/data accessed and stored by the network computing entity 130 to facilitate the operations of the system. More specifically, non-volatile memory 206 may encompass one or more data stores configured to store information/data usable in certain embodiments.

B. Exemplary User Computing Entity

FIG. 3 provides an illustrative schematic representative of user computing entity 110A-110N that can be used in conjunction with various embodiments. As shown in FIG. 3, a user computing entity 110A can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a network computing entity 130, another user computing entity 110A, a monitoring device 170, and/or the like. In this regard, the user computing entity 110A may be capable of operating with one or more air interface standards, communication protocols, modulation types, and access types. More particularly, the user computing entity 110A may operate in accordance with any of a number of wireless communication standards and protocols. In a particular embodiment, the user computing entity 110A may operate in accordance with multiple wireless communication standards and protocols, such as GPRS, UMTS, CDMA2000, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 110A can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 110A can also download changes, add-ons, and updates, for instance, to its firmware, software (e.g., including executable instructions, applications, program modules), and operating system.

According to one embodiment, the user computing entity 110A may include location determining aspects, devices, modules, functionalities, and/or similar words used herein interchangeably. For example, the user computing entity 110A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's position in connection with a variety of other systems, including cellular towers, Wi-Fi access points, and/or the like. Similarly, the user computing entity 110A may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE (Bluetooth Low Energy) transmitters, NFC transmitters, and/or the like. These indoor positioning aspects can be used in a variety of settings to determine the location of someone or something to within inches or centimeters.

In various embodiments, the user computing entity comprises one or more processing elements 308 (also referred to as processors, processing circuitry, and/or similar terms used herein interchangeably) that communicate with other elements within the user computing entity 110 via a bus, for example, or network connection. As will be understood, the processing element 308 may be embodied in a number of different ways. For example, the processing element 308 may be embodied as one or more complex programmable logic devices (CPLDs), microprocessors, multi-core processors, coprocessing entities, application-specific instruction-set processors (ASIPs), and/or controllers. Further, the processing element 308 may be embodied as one or more other processing devices or circuitry. The term circuitry may refer to an entirely hardware embodiment or a combination of hardware and computer program products. Thus, the processing element 308 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 308 may be configured for a particular use or configured to execute instructions stored in volatile or non-volatile media or otherwise accessible to the processing element 308. As such, whether configured by hardware or computer program products, or by a combination thereof, the processing element 308 may be capable of performing steps or operations according to embodiments of the present invention when configured accordingly.

The user computing entity 110A may also comprise a user interface device comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 110A to cause display or audible presentation of information/data and for user interaction therewith via one or more user input interfaces. As just one specific example, the user computing entity 110A may be configured to output various interface screens associated with a monitoring application, monitoring dashboard, electronic health record, and/or the like. The user input interface can comprise any of a number of devices allowing the user computing entity 110A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 110A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 110A can collect information/data, user interaction/input, and/or the like.

The user computing entity 110A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions (e.g., with assistance of the processing element 308) of the user computing entity 110A. Again, as a specific example, the user computing entity memory storage areas (encompassing one or both of the volatile memory 322 and/or non-volatile memory 324) may store the monitoring application thereon, which itself may encompass one or more artificial intelligence and/or machine-learning algorithms.

As indicated, in one embodiment, the user computing entity 110 may also include one or more network and/or communications interfaces 320 for communicating with various computing entities, such as by communicating data, content, information, and/or similar terms used herein interchangeably that can be transmitted, received, operated on, processed, displayed, stored, and/or the like. For instance, the user computing entity 110 may communicate with network computing entities 130 or communication interfaces of other computing entities, monitoring device 170, user computing entities 110, and/or the like.

As indicated, in one embodiment, the user computing entity 110 may also include one or more network and/or communications interfaces 320 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as universal serial bus (USB), fiber distributed data interface (FDDI), digital subscriber line (DSL), Ethernet, asynchronous transfer mode (ATM), frame relay, data over cable service interface specification (DOCSIS), or any other wired transmission protocol. Similarly, the user computing entity 110 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The user computing entity 110 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

In some embodiments, the user computing entity 110 may be configured to interface with a monitoring device 170. In various embodiments, the monitoring device 170 comprises a plurality of sensors configured to captures instances of data samples. In various embodiments, the monitoring device 170 comprises processing circuitry configured to process one or more data samples of the instances of data samples captured by the plurality of sensors. In various embodiments, the user computing entity 110 may interface with the monitoring device 170 such that the user computing entity 110 obtains and/or receives the instances of data samples and/or a result of processing one or more data samples of the plurality of data samples by the processing circuitry. In various embodiments, the user computing entity 110 stores the instances of data samples and/or a result of processing one or more data samples of the plurality of data samples by the processing circuitry (and any associated metadata) in volatile and/or non-volatile memory 322, 324 and/or provide the instances of data samples and/or a result of processing one or more data samples of the plurality of data samples by the processing circuitry (possibly in association with corresponding metadata) such that a network computing entity 130 receives the instances of data samples and/or a result of processing one or more data samples of the plurality of data samples by the processing circuitry (and any associated metadata).

C. Exemplary Monitoring Device

In various embodiments, the monitoring device 170 comprises a plurality of sensors 435. The monitoring device 170 may be embodied as a wearable device having one or more sensor arrays incorporated therein, with each sensor array having a plurality of sensors arranged over a particular area of the wearable device, such as an area expected to cover one or more target organs (e.g., heart and/or lungs) when worn by a patient. In various embodiments, the monitoring device 170 further comprises processing circuitry such as sound analysis circuitry 430 and/or a processing element 405. In various embodiments, the monitoring device 170 comprises a communications interface 420 configured to enable the monitoring device 170 to communicate with a user computing entity 110 and/or network computing entity 130 in a wired and/or wireless manner (e.g., via network 120). In various embodiments, the monitoring device 170 may further comprise volatile and/or non-volatile memory 410, 415. In an example embodiment, the monitoring device 170 may further comprise input/output circuitry 425. In various embodiments, the monitoring device 170 is embodied as a wearable device (e.g., a vest) and the sensors 435 are coupled and/or secured to and/or integrated into the wearable portion. For example, the wearable portion may be configured such that when a patient wears the wearable portion, the sensors 435 are located at particular positions on the patient's chest and/or back.

In various embodiments, the sensors 435 comprise one or more audio sensors configured to record and/or digitize sound. For example, the sensors 435 may comprise one or more microphones and/or the like configured to capture sound generated within a patient's body, for example, by the functioning of organs such as the patient's lungs and/or heart. In various embodiments, a plurality of audio sensors are provided and may be arranged in one or more sensor arrays collectively covering an area of the monitoring device 170 (and when in use, an area of the patient's body). For example, each of the plurality of audio sensors may be configured to capture sounds generated by different portions of a patient's organs such as lungs and/or heart. For example, the monitoring device 170 may be configured such that, when in use, audio sensors are positioned at various locations about the patient's chest and back. For example, the various locations about the patient's chest and back may be known and/or traditional auscultation locations (e.g., the aortic valve area, pulmonic valve area, Erb's point, tricuspid valve area, mitral valve area, and/or the like) and/or distributed about the patient's chest and/or back so as to capture a sounds generated from various portions of the patient's organs (e.g., lungs and/or heart). In an example embodiment, one or more audio sensors may be positioned so as to capture background and/or environmental noises, the patient's voice, and/or the like. For example, one or more audio sensors may be disposed on an external surface of a wearable element (e.g., a vest) of the monitoring device 170 for capturing background noises, environment noises, and/or a patient's voice and one or more audio sensors may be disposed on an internal surface of the wearable element for capturing auscultation noises emanating from within the patient. In various embodiments, the sensors 435 comprise pulse and/or heart rate sensors configured to detect a patient's pulse and/or otherwise determine a patient's heart rate and/or track the patient's cardiac cycle. In various embodiments, the sensors 435 comprise stretch sensors configured to monitor the expansion and contraction of a patient's chest as the patient inhales and exhales, and/or the like. In various embodiments, the sensors 435 may comprise other sensors configured to track the patient's respiratory cycle.

As described above the one or more audio sensors, pulse and/or other cardiac cycle tracking sensors, and/or stretch and/or other respiratory cycle tracking sensors may be positioned at particular and reproducible locations of the patient's body (e.g., chest and/or back). For example, the monitoring device 170 may comprise a wearable element having the sensors 435 integrated therein. For example, the monitoring device 170 may comprise a vest having the sensors 435 integrated therein. Thus, the vest may be worn by a patient such that the sensors 435 are in particular and reproducible locations on the patient's body and one or more instances of data samples may be captured. In various embodiments, the processing element 405, volatile memory 410, non-volatile memory 415, communications interface 420, and/or sound analysis circuitry 430 may also be integrated into the wearable element (e.g., vest). An example monitoring device 170 embodied as a wearable device that may be used in accordance with various embodiments is described in more detail in U.S. patent application Ser. No. 17/095,853, filed Nov. 12, 2020, the contents of which are incorporated herein by reference in their entirety.

In various embodiments, the monitoring device 170 comprises sound analysis circuitry 430 configured to process, modify, and/or the like signals generated by the audio sensors that encode the sounds captured by the audio sensors. For example, the sound analysis circuitry 430 may process, modify, and/or the like voltage signals corresponding to and/or generated by digitizing the sounds captured by the audio sensors. For example, the sound analysis circuitry 430 may comprise one or more operational amplifiers or other components that may be used to adjust the phase of a voltage signal. For example, the one or more operational amplifiers or other components may be used to generate an output signal that is 180 degrees out of phase with an input voltage signal. In an example embodiment, the sound analysis circuitry 430 comprises signal combining circuitry used to combine two voltage signals. For example, the signal combining circuitry may be configured to combine a first voltage signal and a third voltage signal, where the third voltage signal is generated by adjusting the phase of a second voltage signal. In an example, embodiment, the signal combining circuitry may be configured to combine an instance of a first voltage signal with another instance of the first voltage signal to generate a doubled amplitude first voltage signal. The sound analysis circuitry 430 may comprise various other components configured to condition, modify, process, adjust, and/or the like various properties of one or more voltage signals encoding sounds captured and/or digitized by the audio sensors.

In various embodiments, the monitoring device 170 comprises input/output circuitry 425. In an example embodiment, the input/output circuitry 425 may comprise a power on/off switch, button, and/or other component. In an example embodiment, the monitoring device 170 may be configured to receive user input and/or provide output to a user via a connected user computing entity 110 (e.g., a user computing entity 110) in wired or wireless communication with the monitoring device 170.

In an example embodiment, the input/output circuitry 425 comprises a user interface device comprising one or more user input/output interfaces (e.g., a display and/or speaker/speaker driver coupled to a processing element 405 and a touch screen, keyboard, mouse, and/or microphone coupled to a processing element 405). For example, the user output interface may be configured to provide an user interface used to provide instructions regarding a particular word a patient should speak, a particular manner in which a patient should breath or move their body, a particular body position a patient should assume, and/or the like while additional instances of data samples are being captured. In another example, the user output interface may be configured to provide feedback when instances of data samples have been captured and a monitoring session has been completed. The user input interface can comprise any of a number of devices allowing the monitoring device 170 to receive data, such as a keypad (hard or soft), a touch display, voice/speech or motion interfaces, scanners, readers, or other input device. In embodiments including a keypad, the keypad can include (or cause display of) the conventional numeric (0-9) and related keys (#, *), and other keys used for operating the monitoring device 170 and may include a full set of alphabetic keys or set of keys that may be activated to provide a full set of alphanumeric keys. In addition to providing input, the user input interface can be used, for example, to activate or deactivate certain functions, such as capturing of instances of data samples and/or the like. Through such inputs the monitoring device 170 can collect information/data, user interaction/input, and/or the like.

In various embodiments, the monitoring device 170 comprises one or more processing elements 405 (also referred to as processors, processing circuitry, and/or similar terms used herein interchangeably) that communicate with other elements within the monitoring device 170 via a bus, for example, or network connection. As will be understood, the processing element 405 may be embodied in a number of different ways. For example, the processing element 405 may be embodied as one or more complex programmable logic devices (CPLDs), microprocessors, multi-core processors, coprocessing entities, application-specific instruction-set processors (ASIPs), and/or controllers. Further, the processing element 405 may be embodied as one or more other processing devices or circuitry. The term circuitry may refer to an entirely hardware embodiment or a combination of hardware and computer program products. Thus, the processing element 405 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 405 may be configured for a particular use or configured to execute instructions stored in volatile or non-volatile media or otherwise accessible to the processing element 405. As such, whether configured by hardware or computer program products, or by a combination thereof, the processing element 405 may be capable of performing steps or operations according to embodiments of the present invention when configured accordingly.

The monitoring device 170 can also include volatile storage or memory 410 and/or non-volatile storage or memory 415, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions (e.g., with assistance of the processing element 405) of the user computing entity 110A. Again, as a specific example, the user computing entity memory storage areas (encompassing one or both of the volatile memory 410 and/or non-volatile memory 415) may store the monitoring application thereon, which itself may encompass one or more artificial intelligence and/or machine-learning algorithms.

As indicated, in one embodiment, the monitoring device 170 may also include one or more network and/or communications interfaces 420 for communicating with various computing entities, such as by communicating data, content, information, and/or similar terms used herein interchangeably that can be transmitted, received, operated on, processed, displayed, stored, and/or the like. For instance, the monitoring device 170 may communicate with a user computing entity 110, network computing entities 130, and/or the like.

As indicated, in one embodiment, the monitoring device 170 may also include one or more network and/or communications interfaces 420 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as USB, FDDI, DSL) Ethernet, ATM, frame relay, DOCSIS, or any other wired transmission protocol. Similarly, the monitoring device 170 may be configured to communicate via wireless external communication networks using any of a variety of protocols, such as GPRS, UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR protocols, NFC protocols, Wibree, Bluetooth protocols, wireless USB protocols, and/or any other wireless protocol. The monitoring device 170 may use such protocols and standards to communicate using BGP, DHCP, DNS, FTP, HTTP, HTTP over TLS/SSL/Secure, IMAP, NTP, SMTP, Telnet, TLS, SSL, IP, TCP, UDP, DCCP, SCTP, HTML, and/or the like.

IV. Exemplary System Operation

The operation of various embodiments of the present invention will now be described. As discussed herein, various embodiments are directed to systems and methods for the automated detection and/or identification of suspect sounds in captured auscultation audio samples corresponding to the functioning of a patient's lungs and/or heart.

In various embodiments, a monitoring device 170 comprising a plurality of sensors 435 is positioned with respect to a patient's body. For example, the monitoring device 170 may comprise a wearable portion, such as a vest, that having the plurality of sensors 435 integrated therein and/or secured thereto. For example, the wearable portion may comprise a plurality of audio sensors configured for capturing auscultation audio samples, patient speaking audio samples, background/environment noise audio samples, and/or the like. In various embodiments, the monitoring device 170 further comprises sensors configured to capture signals that may be used for tracking a patient's respiratory and/or cardiac cycle. For example, a pulse sensor may track the patient's pulse as an indicator of the patient's cardiac cycle. In another example, a stretch sensor (e.g., comprising a strain gauge) may measure a stretch of the wearable portion of the monitoring device as the patient's chest expands and contracts as the patient inhales and exhales as an indicator of the patient's respiratory cycle. One or more instances of data samples may be captured by the plurality of sensors 435. In various embodiments, an instance of data samples comprises auscultation audio samples and possibly signals tracking the patient's respiratory and/or cardiac cycle that were captured simultaneously, at the same time, and/or in real time with respect to one another.

In various embodiments, the monitoring device 170 may be in communication with a user computing entity 110 and/or a network computing entity 130. In various embodiments, the monitoring device 170 is in wired or wireless communication with a user computing entity 110 co-located (e.g., within the same room) as the monitoring device 170. In an example embodiment, a user computing entity 110 may operate a monitoring application (e.g., stored in memory 322, 324 and executed by processing element 308) that may be configured and/or programmed to control one or more functions of a monitoring device 170 in communication with the user computing entity 110 (e.g., via communication interfaces 420, 320). In an example embodiment, a user computing entity 110 and/or a network computing entity 130 may receive and/or obtain one or more instances of data samples and possibly corresponding metadata and execute a monitoring application to perform analysis and/or processing of the one or more instances of data samples. For example, the monitoring device 170 may capture an instance of data samples and provide the instance of data samples to a co-located user computing entity 110. The co-located user computing entity 110 may process and/or analyze the instance of data samples and identify any suspect sounds present therein. The co-located user computing entity 110 may then provide (via a user interface thereof) instructions regarding patient movement, body positioning, and/or speaking during the capturing of additional instances of data samples and cause the monitoring device 170 to cause the capturing of the additional instances of data samples. The user computing entity 110 may then analyze and/or process the additional instances of data samples. The results of the analysis and/or processing of the instances of data samples and/or the additional instances of data samples may be stored (e.g., in memory 324 and/or provided such that the network computing entity 130 receives the results of the analysis and/or processing of the instances of data samples and/or the additional instances of data samples. In an example embodiment, the user computing entity 110 may also store and/or provide the instances of data samples and/or additional instances of data samples (possibly in association with corresponding metadata). The network computing entity 130 may store the received results and/or instances of data samples and/or additional instances of data samples (and any associated metadata) in, for example, an electronic health record and/or provide the received results and/or instances of data samples and/or additional instances of data samples (and associated metadata) for review by a physician or other healthcare worker via a monitoring dashboard.

In another example embodiment, the monitoring device 170 may capture an instance of data samples; process and/or analyze the instance of data samples to identify any suspect sounds present therein; provide (via a user interface thereof) instructions regarding patient movement, body positioning, and/or speaking during the capturing of additional instances of data samples; capture the additional instances of data samples; analyze and/or process the additional instances of data samples; and store and/or provide the instance of data samples, additional instances of data samples, results of the analysis and/or processing of the instances of data samples and/or the additional instances of data samples, and any associated metadata. A user computing entity 110 and/or the network computing entity 130 may receive and/or provide the instance of data samples, additional instances of data samples, results of the analysis and/or processing of the instances of data samples and/or the additional instances of data samples, and any associated metadata and store (e.g., in respective memory 206, 207, 322, 324) and/or provide at least a portion of the receive information for review by a physician or other healthcare worker via a monitoring dashboard, for example.

Thus, in various embodiments, a user computing entity 110 may control a monitoring device 170 with which the user computing entity 110 is in communication with via execution, by the processing element 308 of a monitoring application. In various embodiments, the monitoring device 170 is a standalone, and possibly dedicated, device that may be configured to communicate information/data to/from a user computing entity 110 and/or network computing entity 130. In various embodiments, the analysis and/or processing of an instance of data samples and/or an additional instance of data samples may be performed by the monitoring device 170, a user computing entity 110, or a network computing entity 130.

A. Example Identifying and Providing of Suspect Sounds

FIG. 5 provides a flowchart of processes, procedures, operations, and/or the like for conducting a monitoring session to identify any suspect sounds present in auscultation audio samples corresponding to functioning of a patient's lungs and/or heart and providing information/data regarding any identified suspect sounds. FIG. 5 will be discussed with reference to the processing and analysis of the instances of data samples being processed by the monitoring device 170. However, as should be understood, the monitoring device 170 may capture instances of data samples and provide the instances of data samples to the user computing entity 110 or network computing entity 130 for processing and/or analysis (e.g., via communications interfaces 420, 320, 208).

Starting at step/operation 502, one or more instances of data samples are obtained. For example, the monitoring session may be initiated by positioning the plurality of sensors 435 of the monitoring device 170 on the chest and/or back of a patient and providing input to the monitoring device 170 (e.g., via input/output circuitry 425) that a monitoring session should be conducted. For example, the monitoring device 170 may be embodied as a wearable device comprising a wearable portion, such as a vest, that may be put on to the patient so as to cause the plurality of sensors 435 integrated into and/or secured to the wearable portion to be properly positioned with respect to the patient's chest and/or back. Once the plurality of sensors are properly positioned with respect to the patient's chest and/or back and the user input indicating a monitoring session should be conducted is received, the monitoring device 170 may control the plurality of sensors 435 to capture one or more instances of data samples and provide the instances of data samples such that the processing element 405 obtains one or more instances of data samples. For example, a monitoring application (e.g., stored in volatile or non-volatile memory 410, 415) may be executed by the processing element 405 to cause one or more instances of data samples to be captured by the plurality of sensors 435 and obtained by the processing element 405.

In various embodiments, an instance of data samples comprises at least two auscultation audio samples captured at different positions of a patient's chest and/or back, optionally signals tracking the patient's respiratory and/or cardiac cycle, and optionally background/environment audio samples that were captured simultaneously, at the same time, and/or in real time with respect to one another. The auscultation audio samples comprise audio and/or sounds generated by the functioning of the patient's heart and/or lungs. In various embodiments, an auscultation audio sample may be represented by a voltage signal or other digitized signal generated by an audio sensor in response to detecting and/or having sounds (e.g., pressure waves) incident thereon. In an example embodiment, each auscultation audio sample is associated with a sensor identifier such that the location of the sensor 435 that captured the auscultation audio sensor may be known and/or determined based on the associated sensor identifier. An example of a signal tracking a patient's cardiac cycle is a signal corresponding to the patient's pulse. An example of a signal tracking a patient's respiratory cycle is a signal corresponding to the expanding and contraction of the patient's chest as the patient inhales and exhales (e.g., as measured by a stretch sensor). In an example embodiment, an instance of data samples may be associated with metadata such as a date and/or time at which the data samples of the instance of data samples were captured; information/data corresponding to the location of each of the audio sensors on the patient's chest and/or back; context information such as a body position, breathing manner, movement, and/or word being spoken by the patient as the data samples of the instance of data samples were captured; a temporal length of the data samples of the data samples; a name and/or other patient identifier identifying the patient and/or an electronic health record corresponding to the patient; and/or the like.

At step/operation 504, the auscultation audio samples from at least one of the one or more instances of data samples are processed and/or analyzed to determine if any suspect sounds are present in the auscultation audio samples and/or to identify any suspect sounds present in the auscultation audio samples. In an example embodiment, at least a portion of the processing and/or analyzing of the auscultation audio samples is performed using the sound analysis circuitry 430. For example, the processing element 405 may process and/or analyze one or more auscultation audio samples of an instance of data samples to determine whether any suspect sounds are present in the auscultation audio samples and/or identify any suspect sounds that are present in the auscultation audio samples. For example, the processing element 405 may cause the sound analysis circuitry 430 to perform at least a portion of the processing and/or analyzing the one or more auscultation audio samples. In an example embodiment, processing the auscultation audio samples includes modifying the phase of at least one auscultation audio sample (and/or a voltage signal representing the at least one auscultation audio sample) and combining the at least one auscultation audio signal (and/or a voltage signal representing the at least one auscultation audio sample) with another one of the auscultation audio samples (and/or a voltage signal representative thereof). For example, such combination of auscultation audio samples may be used to remove background noise from the samples such that any suspect sounds present in the auscultation audio samples is isolated for further analysis. The resultant audio sample (and/or voltage signal representative thereof) may be analyzed and/or the like to determine whether any suspect sounds are present therein and/or to identify any suspect sounds present therein. For example, the processing and/or analyzing of the auscultation audio samples of the instance of data samples results in an isolated sound sample comprising an isolated sample of any suspect sounds present in the auscultation audio samples. An example process that may be used to process and/or analyze auscultation audio samples to isolate and identify any suspect sounds present therein is discussed in more detail elsewhere herein with respect to FIG. 7.

At step/operation 506 it is determined whether any suspect sounds were identified within the auscultation audio samples of an instance of data samples. For example, the processing element 405 may determine whether any suspect sounds are present within the auscultation audio samples of the instance of data samples. In an example embodiment, a machine learning-trained model (e.g., a classifier, neural network, and/or the like) may receive the isolated sound sample as input and analyze the isolated sound sample to determine whether any suspect sounds are present in the isolated sound sample and/or identify any suspect sounds present in the isolated sound sample. In an example embodiment, one or more frequency criteria (embodied as bandpass filters, in an example embodiment) and/or timing criteria are used to determine whether any suspect sounds are present in the isolated sound sample and/or identify any suspect sounds present in the isolated sound sample.

In an example embodiment, a machine learning-trained model (e.g., a classifier, neural network, and/or the like), such as a criteria model, may analyze the isolated sound sample based on one or more frequency criteria and/or timing criteria to determine whether any suspect sounds are present in the isolated sound sample and/or identify any suspect sounds present in the isolated sound sample. In an example embodiment, the one or more frequency and/or timing criteria may be generated by and/or periodically adjusted by a machine learning-trained model using a supervised machine learning or semi-supervised machine learning technique. For example, the criteria model may be trained using isolated sound samples from patients known to have health conditions corresponding to the functioning of the heart and/or lungs and/or isolated sound samples known to include, and associated with corresponding labels, suspect sounds (e.g., as determined by a physician or other auscultation-trained health worker). For example, the criteria model may be further trained using isolated sound samples from patients known to have healthy functioning organs (e.g., heart and/or lungs) and/or known to not include a suspect sound (e.g., as determined by a physician or other auscultation-trained health worker). Re-training and/or additional training of the criteria model may occur periodically based on physician and/or healthcare worker confirmation and/or feedback regarding the automated determinations regarding identifying suspect sounds in isolated sound samples. For example, a physician may review (e.g., via a monitoring dashboard) the automated determination of an isolated sound sample including or not including a particular suspect sound and provide feedback to the system regarding whether the physician agrees with the automated determination. This feedback may be used to regularly, occasionally, and/or periodically updating the criteria model (e.g., re-training and/or further training the criteria model). In various embodiments, training (and/or re-training and/or further training) of the criteria model may cause determinations of which frequency and/or timing criteria correspond to which types of suspect sounds and/or health conditions and/or generation of frequency and/or timing criteria that may be used to identify particular suspect sounds and/or corresponding health conditions by analyzing an isolated sound sample based on the frequency and/or timing criteria.

When, at step/operation 506, it is determined that there are not any suspect sounds present in the auscultation audio samples based on the content of the isolated audio sample, the process continues to step/operation 508. At step/operation 508, the analyzed instance(s) of data samples are marked, flagged, and/or the like as not containing any suspect sounds. In an example, embodiment, the processing element 405 may mark, flag, and/or the like the analyzed instance(s) of data samples as not containing any suspect sounds. In an example embodiment, an instance of monitoring results corresponding to the analyzed instance(s) of data samples are stored (e.g., in memory 410, 415) and/or provided (e.g., via communications interface 420, input/output circuitry 425, and/or the like). In an example embodiment, an instance of monitoring results may comprise the corresponding analyzed instance(s) of data samples, the isolated sound sample, metadata corresponding to the analyzed instance(s) of data samples, metadata (e.g., a mark, flag, and/or other indication) indicating that no suspect sounds were identified in the auscultation audio samples, and/or other information/data and/or results of analyzing the analyzed instance(s) of data samples. In an example embodiment, the instance of monitoring results is provided such that a user computing entity 110 and/or network computing entity 130 receives the instance of monitoring results (e.g., in memory 206, 207, 322, 324) and/or provides the instance of monitoring results (e.g., via communications interface 208, 320, input/output circuitry 216, display 316, and/or the like). For example, a user computing entity 110 and/or network computing entity 130 may store at least a portion of the instance of monitoring results in a database and/or as part of an electronic health record corresponding to the patient. For example, the user computing entity 110 and/or network computing entity 130 may provide the at least a portion of the instance of monitoring results via a monitoring dashboard, such as the example monitoring dashboard 600 screen view shown in FIG. 6.

When, at step/operation 506, it is determined that a suspect sound is present in the auscultation audio samples based on the content of the isolated sound sample, the process continues to step/operation 510. At step/operation 510, the monitoring device 170 provides instructions for capturing additional instances of data samples. For example, based on the suspect sound identified in the isolated sound sample and/or determined to be present in the auscultation audio samples, one or more contexts for additional instances of data samples to be captured may be identified. A context for an instance of data samples comprises a body position of the patient while the instance of data samples is captured, a manner of breathing (e.g., normal breathing, deep breathing, and/or the like) of the patient while the instance of data samples is captured, whether the patient is speaking or not and, if the patient is speaking, the word the patient is speaking while the instance of data samples is captured, whether the patient is moving or being still, and if the patient is moving, the manner in which the patient is moving, while the instance of data samples is captured, and/or the like. In various embodiments, the contexts identified for a suspect sound may be configured to emphasize the identified suspect sound, emphasize a representation of disorder associated with the suspect sound, and/or the like in an instance of data samples captured in accordance with a respective context. For example, a suspect sound may be associated with disorder A and disorder B; however, disorder A may be emphasized under context A and disorder B may be emphasized under context B. Thus, the contexts A and B may be identified so as to better identify, distinguish, diagnose, and/or the like the specific disorder present in the patient. In an example embodiment, a (machine learning-trained) context selection model (e.g., operating on processing element 405) may determine the context(s) under which one or more additional data samples should be captured.

The processing element 405 may cause instructions regarding a context to be provided via input/output circuitry 425 of the monitoring device 170. For example, the instructions may indicate the intended context for an additional instance of data samples to be captured. For example, the instructions may comprise an indication (verbal and/or visual) of a body position the patient should assume for the capturing of an additional instance of data samples. For example, the instructions may comprise an indication (verbal and/or visual) of a word the patient should speak and/or a manner with which the patient should breath for the capturing of an additional instance of data samples. For example, the instructions may comprise an indication (verbal and/or visual) of a movement the patient should do for the capturing of an additional instance of data samples.

In an example embodiment, the instructions associated with one or more contexts are stored in memory (e.g., volatile memory 410, non-volatile memory 415) and indexed based on elements of the corresponding context. In an example embodiment, the instructions for a context are generated in real-time and/or near real-time with respect to the provision of the instructions via the input/output circuitry 425. In an example embodiment, the instructions for a context are generated based at least in part on stored instruction elements that correspond to possible options for one or more elements. For example, if the context is sitting still and saying the word "dog," the instructions may be generated from a stored instruction element corresponding to sitting, a stored instruction element corresponding to being still, and a stored instruction element corresponding to saying a word or saying the word "dog." In an example embodiment, the patient may be instructed to speak more loudly, more softly, faster, slower, and/or the like; move faster or slower; and/or the like.

At step/operation 512, the sensors 435 may capture one or more additional instances of data samples. In an example embodiment, the processing element 405 may monitor signals provided by one or more sensors 435 to determine when the patient is in and/or performing the context in accordance with the provided instructions (e.g., an audio sensor configured to capture the patient's voice may capture sound indicating that the patient is speaking a particular word in accordance with the instructions or a motion sensor may indicate the that the patient is moving (or not moving) in accordance with the instructions) and, responsive to determining the that the patient is in and/or performing the context in accordance with the provided instructions, cause one or more additional instances of data samples to be captured. In an example embodiment, a subset of the sensors 435 may be used to capture the one or more additional instances of data samples based on a type of the identified sound and/or the location within the patient's body where the identified suspect sound originated. The processing element 405 may obtain the one or more additional instances of data samples.

Similar to the instances of data samples obtained in step/operation 502, an additional instance of data samples comprises at least two auscultation audio samples captured at different positions of a patient's chest and/or back, optionally signals tracking the patient's respiratory and/or cardiac cycle, and optionally background/environment audio samples that were captured simultaneously, at the same time, and/or in real time with respect to one another and may be associated with metadata.

At step/operation 514, the additional instances of data samples may be processed and/or analyzed to extract, identify, isolate, and/or the like any suspect sounds present therein. For example, the auscultation audio samples from at least one of the one or more additional instances of data samples are processed and/or analyzed to determine if any suspect sounds are present in the auscultation audio samples, to identify any suspect sounds present in the auscultation audio samples, to extract suspect sounds from the auscultation audio samples, and/or to generate isolated sound samples comprising the suspect sounds from the auscultation audio samples. In an example embodiment, at least a portion of the processing and/or analyzing of the auscultation audio samples is performed using the sound analysis circuitry 430. For example, the processing element 405 may process and/or analyze one or more auscultation audio samples of an instance of data samples to determine whether any suspect sounds are present in the auscultation audio samples, identify any suspect sounds that are present in the auscultation audio samples, to extract suspect sounds from the auscultation audio samples, and/or to generate isolated sound samples comprising the suspect sounds from the auscultation audio samples. For example, the processing element 405 may cause the sound analysis circuitry 430 to perform at least a portion of the processing and/or analyzing the one or more auscultation audio samples. In an example embodiment, processing the auscultation audio samples includes modifying the phase of at least one auscultation audio sample (and/or a voltage signal representing the at least one auscultation audio sample) and combining the at least one auscultation audio signal (and/or a voltage signal representing the at least one auscultation audio sample) with another one of the auscultation audio samples (and/or a voltage signal representative thereof). For example, such combination of auscultation audio samples may be used to remove background noise from the samples such that any suspect sounds present in the auscultation audio samples are isolated for further analysis. The resultant audio sample (and/or voltage signal representative thereof) may be analyzed and/or the like to determine whether any suspect sounds are present therein and/or to identify any suspect sounds present therein. For example, the processing and/or analyzing of the auscultation audio samples of the instance of data samples results in an isolated sound sample comprising an isolated sample of any suspect sounds present in the auscultation audio samples. An example process that may be used to process and/or analyze auscultation audio samples to isolate and identify any suspect sounds present therein is discussed in more detail elsewhere herein with respect to FIG. 7.

Based on the result from analyzing the one or more additional instances of data samples, the monitoring device 170 (e.g., via execution of a monitoring application by the processing element 405) may determine whether additional instances of data samples should be captured. For example, it may be determined that an additional instance of data samples should be captured under a different context. In another example, it may be determined that the isolated sound sample captured under a particular context did match expectations and another additional instance of data samples should be captured under the particular context. Thus, in various embodiments, the process may return to step/operation 510.

In various embodiments, the determination of which additional instances of data samples and/or under which contexts additional instances of data samples should be captured may be performed by a machine learning-trained model. For example, a machine learning-trained model, such as a classifier, neural network (e.g., recurrent neural network, convolutional neural network, a neural network with a self-attention mechanism, and/or the like), deep net, and/or the like may be configured to be a context selection model. In an example embodiment, the context selection model may be specific to a particular type of suspect sound (e.g., wheeze, rhonchi, stridor, fine crackle, coarse crackle, pleural rub, squawk, gasp, and/or the like). For example, the context selection model may be selected based on a type of the suspect sound identified at step/operation 506, in an example embodiment. In an example embodiment, the context selection model may be configured to under which contexts additional instance of data samples should be captured and perform analysis of the captured additional instances of data samples for multiple types of suspect sounds. For example, the context selection model may receive as input a type of the suspect sound identified at step/operation 506, in an example embodiment. In various embodiments, the context selection model may be configured and/or trained to select contexts under which additional instances of data samples are captured based on analysis of the already captured instances of data samples (which may include previously captured additional instances of data samples) to determine which contexts additional instances of data samples should be captured under in order to generate auscultation audio samples and/or isolated sound samples to emphasize the identified suspect sound, emphasize a representation of disorder associated with the suspect sound, provide the best diagnostic information/data, and/or the like in an instance of data samples captured in accordance with a respective context. For example, based on the intensity, continuity, duration, timing, pitch, quality, and/or the like of the identified suspected sounds and causes and/or diseases/health conditions associated with the suspect sounds identified based on analysis and/or processing of previously captured instances of data samples (which may include previously captured additional instances of data samples) the content selection model may determine whether more additional instances of data samples should be captured and under what contexts those additional instances of data samples should be captured.

In an example embodiment, the context selection model is trained using a supervised or semi-supervised machine learning technique based on results of analyzing and/or processing instances of data samples captured under different contexts and/or physician or other healthcare worker feedback. For example, the context selection model may be trained using isolated sound samples with each isolated sound sample associated with metadata indicating a context under which the isolated sound sample was identified and, possibly, a suspect sound present and/or detected in the isolated sound sample and/or a health condition of a patient from which the corresponding instance of data samples was captured. The context selection model may then be trained to determine which contexts provide the most pronounced suspect sounds. In an example embodiment, the context selection model may be trained to determine which contexts provide the most pronounced suspect sounds for various health conditions. For example, health conditions A and B may both be associated with a crackle. However, the context selection model may be trained to identify that under context A, a patient having health condition A will tend to generate a strong crackle, but a patient having health condition B will tend to generate a mild crackle. However, under context B, a patient having health condition B will tend to generate a strong crackle. Thus, the context selection model may be trained to capture additional instances of data samples under different contexts to differentiate which health condition is likely present in a patient and which contexts are likely to lead to the capture of an instance of data samples including a pronounced version of a particular suspect sound.

In various embodiments, the context selection model may be configured to determine that no more additional instances of data samples are to be captured at the present time when an isolated sound sample satisfies a quality threshold criteria, when trying additional contexts for capturing additional instances of data samples do not appear to be providing higher quality isolated sound samples, when a particular number of additional sound samples have been captured, when a particular amount of time has passed during the capturing of the instances of data samples and the additional instances of data samples, based on physician and/or user specified criteria and/or temporal sample length, and/or the like.

At step/operation 516, information/data pertaining to the monitoring session is provided. For example, the information/data pertaining to the monitoring session may be provided such that it is stored in memory 410, 415. For example, the information/data pertaining to the monitoring session may be provided via communications interface 420 such that the information/data pertaining to the monitoring session is received by a user computing entity 110 and/or a network computing entity 130. For example, the user computing entity 110 and/or network computing entity 130 may receive the information/data pertaining to the monitoring session. In an example embodiment, a user computing entity 110 and/or network computing entity 130 may store the information/data pertaining to the monitoring session (e.g., in memory 206, 207, 322, 324), possibly in association and/or as part of an electronic health record. For example, the information/data pertaining to the monitoring session may comprise one or more patient identifiers that may be used to identify an electronic health record corresponding to the patient. The information/data pertaining to the monitoring session may then be stored in association with and/or as part of the electronic health record identified based on the one or more patient identifiers. In an example embodiment, the user computing entity 110 and/or network computing entity 130 may provide at least a portion of the information/data pertaining to the monitoring session via a monitoring dashboard (e.g., an interactive user interface provided via display 316, input/output circuitry 216, and/or the like). In various embodiments, the user computing entity 110 and/or network computing entity 130 may provide at least a portion of the information/data pertaining to the monitoring session for patient, physician, other healthcare worker, and/or other user review via various means (e.g., via display 316 or other output device of a user computing entity 110, input/output circuitry 216, and/or the like).

In various embodiments, the information/data pertaining to the monitoring session comprises at least a portion of the instances of data samples, a result of processing and/or analyzing the instances of data samples (e.g., an isolated sound sample, diagnosis, identified suspect sound description, and/or the like), at least a portion of any additional instances of data samples, a result of processing and/or analyzing any additional instances of data samples (e.g., an isolated sound sample, diagnosis, identified suspect sound description, and/or the like), metadata corresponding to the instances of data samples and/or any additional instances of data samples, and/or the like. In an example embodiment, an instance of data samples may be associated with metadata such as a date and/or time at which the data samples of the instance of data samples were captured; information/data corresponding to the location of each of the audio sensors on the patient's chest and/or back; context information such as a body position, breathing manner, movement, and/or word being spoken by the patient as the data samples of the instance of data samples were captured; a temporal length of the data samples of the data samples; a name and/or other patient identifier identifying the patient and/or an electronic health record corresponding to the patient; patient oxygen saturation ($SpO_2$) and/or other biometric measurements and indicators corresponding to the patient; and/or other parameters corresponding to the patient and/or the capture of the instance of data samples. In an example embodiment, the information/data pertaining to the monitoring session may include a marker, flag, and/or the like indicating that no suspect sound was identified in the auscultation audio samples captured during the monitoring session, when no suspect sounds were identified, or an identified suspect sound description, when a suspect sound was identified. In various embodiments, the identified suspect sound description may comprise a type of the identified suspect sound (e.g., wheeze, rhonchi, stridor, fine crackle, coarse crackle, pleural rub, squawk, gasp, and/or the like) a continuity of the identified suspect sound (e.g., continuous or discontinuous), a time duration of the identified suspect sound, timing of the identified suspect sound (e.g., during which portion(s) of the cardiac and/or respiratory cycle the suspect sounds were present), pitch of the identified suspect sound (e.g., the frequency and/or cycles per second (Hz) of the suspect sound), a quality of identified suspect sound, a location within the patient's body of the identified suspect sound, a determined/presumptive cause of the identified suspect sound, a disease associated with the identified suspect sound, and/or the like. In an example embodiment, the context selection model may determine and/or generate the identified suspect sound description based on analysis and/or processing of the one or more instances of data samples and/or additional instances of data samples.

In an example embodiment, a monitoring device 170 may be in communication with a user computing entity 110 during a monitoring session. For example, the user computing entity 110 may be executing a monitoring application (e.g., via the processing element 308) to control one or more aspects of the monitoring session (e.g., provide instructions regarding a context for capturing an additional instance of data samples, and/or the like). The user computing entity 110 may receive the instances of data samples and/or additional instances of data samples and may associate metadata with the instances of data samples and/or additional instances of data samples. The user computing entity 110 may then associate metadata (e.g., a patient identifier and/or the like) with the instances of data samples and/or additional instances of data samples based on a user profile stored by the user computing entity 110 (e.g., in memory 322, 324) in association with the monitoring application.

In an example embodiment, if the identified suspect sound satisfies emergency criteria, the monitoring device 170, user computing entity 110, and/or network computing entity 130 may cause an alert to be provided to the patient, physician, other healthcare worker, emergency contact of the patient, emergency services, and/or the like (e.g., via a user computing entity 110 corresponding to the alerted entity). For example, the alert may indicate that the patient should be taken to the emergency room and/or the like. For example, the alert may trigger an ambulance and/or emergency medical technicians (EMTs) being dispatched to the patient's location. In an example embodiment, the alert may instruct the patient to partake in a particular therapy, such as a prescription or over the counter drug, body position, movement, and/or the like and then, possibly, to perform another monitoring session after a particular amount of time. In an example embodiment, the emergency criteria may comprise criteria corresponding to the severity of the identified suspect sound, the type of the identified suspect sound, a change in the identified suspect sound from a previous monitoring session, and/or the like.

B. Exemplary Monitoring Dashboard

As noted above, in various embodiments, at least a portion of the information/data pertaining to a monitoring session may be provided via a monitoring dashboard for patient, physician, other healthcare worker, and/or other authorized user for review. For example, a monitoring dashboard may be provide via display 316 (and/or other output device) of a user computing entity 110. In another example, a monitoring dashboard may be provided via input/output circuitry 216 of a network computing entity 130.

FIG. 6 provides an example screen view of a monitoring dashboard 600. In the illustrated example embodiment, the monitoring dashboard 600 comprises patient information/data 602. In various embodiments, the patient information/data 602 may include information/data identifying the patient, such as a patient name, birthdate, and/or other information/data that a physician or other healthcare worker may use to identify a patient.

The monitoring dashboard 600 further comprises a plurality of session portions 610 (e.g., 610A, 610B, 610C) each comprising information/data pertaining to a monitoring session. Each session portion 610 comprises session identifying information/data 612 (e.g., 612A, 612B, 612C). For example, the session identifying information/data 612 may indicate the date and/or time that a respective monitoring session occurred. In an example embodiment, the session identifying information/data 612 may comprise context information/data, a location where the monitoring session occurred, and/or the like. In an example embodiment, a session portion 610 comprises an identified suspect sound description 614 (e.g., 614A, 614B, 614C). For example, if a suspect sound is not identified during the monitoring session, the corresponding identified suspect sound description 614 may indicate that no suspect sound was identified or may be omitted. In an example embodiment, a session portion 610 may comprise a graphical representation 616 (e.g., 616A, 616B, 616C) of a respective identified suspect sound (e.g., a graphical representation of an isolated sound sample), a graphical representation of an auscultation audio sample, and/or the like. In an example embodiment, a session portion 610 may comprise a selectable element 618 (e.g., 618A, 618B, 618C) that when selected via user interaction (e.g., clicking, selecting, and/or the like) with the monitoring dashboard (e.g., via an input device and/or input circuitry), cause an audible representation of the corresponding identified suspect sound (e.g., the isolated suspect sound sample) and/or an auscultation audio sample to be provided (e.g., via a speaker and/or the like).

In the illustrated example embodiment, a session portion 610 corresponding to a monitoring session in which a suspect sound was identified (e.g., session portion 610C), may include a sound heat map 620 illustrating the location of audio sensors with respect to the patient's body (and/or with respect to the monitoring device 170 shape and/or other configuration) that captured auscultation audio samples, during the corresponding monitoring session, in which suspect sounds were identified. For example, the sound heat map 620 may comprise a plurality of sensor location indicators 622 with relation the patient's body and/or organs (or a generic human body and/or organ location illustration). The sensor location indicators 622 correspond to the audio sensors that captured auscultation audio samples during the corresponding monitoring session. The sound heat map may utilize colors, shapes, and/or other visual identifiers to distinguish between sensors that collected auscultation audio samples indicative of the operation of an organ (e.g., a lung), and those sound sensors that collected audio samples that suggest that the sound sensors were not sufficiently near a particular organ to collect usable data. Moreover, the sound heat map may utilize colors, shapes, and/or other visual indicators to emphasize those audio sensors that collected sound data comprising identified suspect sounds, such as suspect sound location indicators 624. For example, the suspect sound location indicators 624 may indicate the location of the sensors, with respect the patient's body and/or organs during corresponding monitoring session in which the sensors captured auscultation audio samples that included the identified suspect sounds. The suspect sound location indicators 624 may be visually differentiable from the remainder of the sensor location indicators 622. For example, the suspect sound location indicators 624 may be a different size, shape, color, and/or the like then the remainder of the sensor location indicators 622. In an example embodiment, a suspect sound location indicators 624 may be configured to indicate an intensity and/or other feature, parameters, and/or descriptor of the suspect sound identified in an auscultation audio sample captured by the corresponding sensor.

In various embodiments, the monitoring device 170 and the corresponding techniques described herein may be used in various different modes. For example, the monitoring device 170 may be operated in an initial setup mode, a patient use mode, or a medical study mode, in an example embodiment. In various embodiments, the information/data provided through the monitoring dashboard 600 and corresponding to a monitoring session may be dependent on which mode the monitoring device 170 was being operated in and the relationship of the user accessing the monitoring dashboard to the patient. For example, a first monitoring session of a patient may be captured in a patient use mode and a second monitoring session of the patient may be captured in a medical study mode. If a physician associated with the medical study corresponding to the second monitoring session accesses a monitoring dashboard 600, the physician associated with the medical study may view information corresponding to the second monitoring session in a manner that protects patient privacy, but not be able to view information corresponding to the first monitoring session. If a physician that is part of patient care team treating the patient accesses a monitoring dashboard 600, the physician that is part of the patient care team may view information corresponding to the first monitoring session and possibly information corresponding to the second monitoring session as well.

C. Exemplary Analysis of an Instance of Data Samples

In various embodiments, an instance of data samples (or an additional instance of data samples) may be obtained by a processing element 405, 308, 205. The processing element 405, 308, 205 may then analyze and/or process the instance of data samples to determine and/or identify any suspect sounds present in one or more auscultation samples of the instance of data samples. In an example embodiment, the processing element 405, 308, 205 may use sound analysis circuitry 430 and/or other appropriate sound analysis circuitry to perform at least a portion of the analysis and/or processing of the instance of data samples.

FIG. 7 provides a flowchart illustrating various processes, procedures, operations, and/or the like performed by processing element 405, 308, 205 to process and/or analyze an instance of data samples to determine and/or identify suspect sounds present in one or more auscultation audio samples of the instance of data samples. In an example embodiment, the steps/operations shown in FIG. 7 may be performed as at least a portion of step/operation 504.

Starting at step/operation 702, the heart or lung sounds are removed from each of the auscultation audio samples of the instance of data samples. For example, the processing element 405, 308, 205 may remove one of the heart sounds or the lung sounds, and possibly other background/environment sounds (e.g., the sounds of the patient's voice speaking while the (additional) instance of data samples was captured). For example, when suspect heart sounds are being explored, the lung sounds may be removed from the auscultation audio samples. For example, when suspect lung sounds are being explored, the heart sounds may be removed from the auscultation audio samples. For example, the signals of the instance of data samples that enable tracking of the patient's respiratory cycle may be used to determine timing and/or other information/data regarding the patient's respiratory cycle and that the timing and/or other information/data regarding the patient's respiratory cycle may be used to remove lung sounds from the auscultation audio samples, in an example embodiment. For example, the signals of the instance of data samples that enable tracking of the patient's cardiac cycle may be used to determine timing and/or other information/data regarding the patient's cardiac cycle and that timing and/or other information/data regarding the patient's cardiac cycle may be used to remove heart sounds from the auscultation audio samples. In an example embodiment, markers, tags, and/or the like may be injected into an auscultation audio signal when the heart/lung sounds are removed indicating the timing of the cardiac/respiratory cycle with respect to the remaining sound of the auscultation audio sample.

At step/operation 704, one or more primary audio samples are selected from the auscultation audio samples (heart/lung and/or background/environment sound removed) of the instance of data samples. For example, the processing element 405, 308, 205 may select and/or identify one or more primary audio samples from the auscultation audio samples of the instance of data samples. In an example embodiment, the one or more auscultation audio samples selected and/or identified as the one or more primary audio samples are the auscultation audio samples having the most predominate, highest amplitude(s) of the auscultation audio samples of the instance of data samples. For example, the n auscultation audio samples having the highest overall peak amplitude during one or more breathing cycles are selected and/or identified as the primary audio samples. In various embodiments, n is an integer equal to or greater than one.

In an example embodiment, one or more secondary audio samples are also selected from the auscultation audio samples (heart/lung and/or background/environment sound removed) of the instance of data samples. For example, the processing element 405, 308, 205 may select and/or identify one or more secondary audio samples from the auscultation audio samples of the instance of data samples. In an example embodiment, the one or more auscultation audio samples selected and/or identified as the one or more secondary audio samples are the auscultation audio samples having the smallest amplitude(s) of the auscultation audio samples of the instance of data samples. For example, the m auscultation audio samples having the lowest overall peak amplitude during one or more breathing cycles are selected and/or identified as the secondary audio samples. In various embodiments, m is an integer equal to or greater than one. In various instances, the secondary audio samples are captured by sensors 435 that are more distant from the source point of any suspect sound present in the auscultation audio samples of the instance of data samples. In an example embodiment, each auscultation audio sample of the instance of data samples that is not selected and/or identified as a primary audio sample is selected and/or identified as a secondary audio sample.

At step/operation 706, the phase of one or more secondary audio samples may be modified and the modified secondary audio samples may be added to each of the primary audio sample. For example, the phase of one or more secondary audio samples may be modified so that the modified secondary audio sample is 180 degrees out of phase with the corresponding secondary audio sample. The modified secondary audio sample may then be added and/or mixed with each of the primary audio samples to generate a current baseline sample. For example, the sound analyzing circuitry 430 or other appropriate sound analyzing circuitry may be used to modify the phase of a secondary audio sample so that a voltage signal representing and/or corresponding to the modified secondary audio sample is 180 degrees, for example, out of phase with a voltage signal representing and/or corresponding to the secondary audio sample. In an example embodiment, an operational amplifier is used to modify the phase of one or more secondary audio samples. In an example embodiment, mixer or multiplexer is used to add and/or mix the modified secondary audio samples with a primary audio sample. In various embodiments, the modified secondary audio sample(s) are added and/or mixed with each of the primary audio samples without performing any alignment functions, processes, and/or the like between the modified secondary audio sample and the primary audio sample.

In various embodiments, the adding and/or mixing of the modified secondary audio samples and the primary audio sample may generate a current baseline sample having normal heart/lung sounds at least partially removed therefrom. For example, the secondary sound samples may comprise normal heart/lung sounds for the patient and the primary audio samples may comprise normal heart/lung sounds in addition to any suspect sounds. The modified secondary audio sample may comprise the normal heart/lung sounds but has been modified so that the phase of the voltage signal representing those normal heart/lung sounds is different (e.g., 180 degrees out of phase) with the voltage signal representing and/or comprising the normal heart/lung sounds of the primary audio sample. Thus, by adding the modified secondary audio samples to a primary audio sample, the normal heart/lung sounds may be at least partially removed from the primary audio sample.

At step/operation 708, the current primary baseline sample may be provided for storage and/or use in future analysis and/or processing of instances of data samples. For example, the processing element 405, 308, 205 may cause the current primary baseline sample to be stored in a corresponding memory 410, 415, 322, 324, 206, 207 for future reference and/or use. In an example embodiment, the current baseline sample may be provided (e.g., via a communications interface 420, 320, 208) such that the current baseline sample and corresponding metadata may be stored in association with an electronic health record corresponding to the patient. The processing element 405, 308, 205 may also determine whether a previous baseline sample is stored in the corresponding memory 410, 415, 322, 324, 206, 207 and, when a previous baseline sample is available, access the previous baseline sample from the corresponding memory.

At step/operation 710, when a previous baseline sample is available, the previous baseline sample may be modified and added to the current baseline sample to generate an isolated sound sample. For example, the phase of the previous baseline sample may be modified and the modified previous baseline sample may be added to the current baseline sample. For example, the phase of the previous baseline sample may be modified so that the modified previous baseline sample is 180 degrees out of phase with the corresponding previous baseline sample. The modified previous baseline sample may then be added and/or mixed with the current baseline sample to generate an isolated sound sample. For example, the sound analyzing circuitry 430 or other appropriate sound analyzing circuitry may be used to modify the phase of the previous baseline sample so that a voltage signal representing and/or corresponding to the modified previous baseline sample is 180 degrees, for example, out of phase with a voltage signal representing and/or corresponding to the previous baseline sample. In an example embodiment, an operational amplifier is used to modify the phase of the previous baseline sample. In an example embodiment, mixer or multiplexer is used to add and/or mix the modified previous baseline sample with a current baseline sample. When a previous baseline sample is not available, the current baseline sample may be used as the isolated suspect sound sample.

In various embodiments, the modified previous baseline sample is added and/or mixed with current baseline sample without performing any alignment functions, processes, and/or the like between the modified previous baseline sample and the current baseline sample. In an example embodiment, the modified previous baseline sample may be aligned with the current baseline sample before the modified previous baseline sample and the current baseline sample are added and/or mixed. For example, a zero-crossing axis may be used as a reference to align the modified previous baseline sample and the current baseline sample. In an example embodiment, in addition to a zero-crossing axis reference alignment, the modified previous baseline sample may be further modified to match the amplitude rise and fall voltage of the current baseline sample. In an example embodiment, audio compression and/or expansion circuits may be used to align the modified previous baseline sample and the current baseline sample along the bandwidth axis of the samples at the beginning 50% rise and the ending 50% fall to provide samples that are matched in bandwidth. In an example embodiment, phase bandwidth shift and/or amplitude variance techniques may be used to adjust the phase and/or amplitude (up to +/−5%, for example) to adjust for maximum quieting in the resultant isolated sound sample.

At step/operation 712, the isolated sound sample is added and/or mixed with itself. For example, the processing element 405, 308, 205 may cause the sound analysis circuitry 430 or other appropriate circuitry to add and/or mix the isolated sound sample with itself. For example, a multiplexer and/or mixer may be used to add to instances of the isolated sound sample. In an example embodiment, no alignment functions, processes, and/or the like are performed. In various embodiments, adding the isolated sound sample to itself may increase the amplitude of any suspect sounds present in the isolated sound sample without introducing various artifacts, smoothing, and/or the like from volume increasing and/or amplifying processes. In various scenarios this increase in the amplitude of the isolated sound sample, which is free of the artifacts and smoothing effects of volume increasing and/or amplifying processes, may enable detection of suspect sounds that are not loud enough to be detected by the human ear during physician performed auscultation.

At step/operation 714, breathing and/or heartbeat timing information/data may be associated with the isolated sound sample. For example, the processing element 405, 308, 205 may inject and/or otherwise associate breathing and/or heartbeat timing information/data into the isolated sound sample. For example, based on the signals comprising information/data for tracking the cardiac and/or respiratory cycle of the patient when the instance of data samples was captured, the isolated sound sample may be annotated to indicate a portion of the cardiac and/or respiratory cycle that corresponds to each signal value of the isolated sound sample. For example, the beginning and/or end of each portion of the cardiac and/or respiratory cycle may be marked in the isolated sound sample. In another example, the beginning and/or end of each cardiac and/or respiratory cycle may be marked in the isolated sound sample.

At step/operation 716, frequency and/or timing criteria are used to determine whether any suspect sounds are present in the isolated sound sample and/or to identify any suspect sounds present in the isolated sound sample. For example, the processing element 405, 308, 205 may use frequency and/or timing criteria to determine whether any suspect sounds are present in the isolated sound sample and/or to identify any suspect sounds present in the isolated sound sample. In an example embodiment, the frequency criteria may comprise one or more bandpass filters and the isolated sound sample may satisfy a bandpass filter when the isolated sound sample comprises a signal having a characteristic frequency that is passed by the bandpass filter. In various embodiments, the bandpass filters may comprise a hardware (e.g., circuit) based filter, a software-based filter, or a combination thereof. For example, an isolated sound sample may satisfy a frequency criteria when a signal in the isolated sound sample has a characteristic frequency that is within the frequency band passed by the bandpass filter. For example, an isolated sound sample may satisfy a frequency criteria and a corresponding timing criteria when a portion of the isolated sound sample that is pass by the bandpass filter of the frequency criteria satisfies the corresponding timing criteria.

In an example embodiment, the timing criteria may relate to the time duration of a sound and/or when during the cardiac/respiratory cycle. For example, an isolated sound sample may satisfy a timing criteria when a signal in the isolated sound sample has a time duration within a time range defined by the timing criteria. For example, an isolated sound sample may satisfy a timing criteria when a signal in the isolated sound sample is present during one or more specified portions of the cardiac/respiratory cycle. In an example embodiment, continuity criteria may also be used to determine whether a suspect sound is present and/or to identify a suspect sound present in an isolated sound sample. In an example embodiment, an isolated sound sample satisfies a continuity criteria when a sound is discontinuous and/or continuous, as specified by the continuity criteria. For example, intermittent, peak, and/or pulse patterns of the isolated sound sample may be detected using frequency to voltage conversion.

In various embodiments, frequency, timing (duration and/or location within a cardiac/respiratory cycle), and/or continuity criteria may be associated with one another and/or combined to identify particular types and/or characteristics of a suspect sound. Various spectrum analysis techniques may be used to dissect the isolated sound sample to determine whether any suspect sounds are present and/or to identify any suspect sounds present in the isolated sound sample. For example, the criteria model may analyze a first portion of the spectrum of the isolated sound sample to determine whether a timing and/or continuity pattern exists in the first portion of the spectrum that is associated with and/or indicative of a particular suspect sound, health condition, and/or the like. A second portion of the spectrum of the isolated sound sample may be analyzed to determine whether different timing and/or continuity patterns are present therein to determine whether a suspect sound is present in the isolated sound sample and/or to identify a suspect sound present in the isolated sound sample.

In an example embodiment, feedback may be used to adjust each frequency band of sound during analysis of peaks of the isolated sound sample via dynamic adjustment of the zero axis sync. For example, the phase shifting and/or axis alignment of the modified previous baseline sample may be adjusted a few degrees either direction and then the modified previous baseline sample would be combined with the current baseline sample to determine and/or further analyze the resulting isolated sound sample for a buried suspect sound that may be indicative of disease and/or poor/mis-function of an organ of the patient. For example, the criteria model may be configured and/or trained to adjust frequency bands of sound during analysis of peaks of the isolated sound sample via dynamic adjustment of the zero axis sync to identify any suspect sounds present in the suspect sound sample that are not within the currently defined frequency bandpasses.

In various embodiments, each frequency, timing, and/or continuity criteria is associated with at least one specified suspect sound, disease, health condition, health state, physical cause, and/or the like. For example, if an isolated sound sample satisfies a particular frequency criteria and a particular timing criteria, and the particular frequency criteria and the particular timing criteria are associated with one or more specified suspect sounds and/or health conditions, it may be determined that the specified suspect sound has been identified in the isolated sound sample and/or that the one or more health conditions may be present in the patient.

In various embodiments, a machine learning-trained model, referred to as the criteria model herein, is trained to use the frequency, timing, continuity, and/or other criteria to determine whether a suspect sound is present and/or identify a suspect sound present in the isolated sound sample. For example, the frequency, timing, continuity and/or other criteria may be generated, updated, modified, adjusted, and/or the like by a criteria model trained to improve identification of suspect sounds from isolated sound samples. As described above, the criteria model may be trained using isolated sound samples from patients known to have health conditions corresponding to the functioning of the heart and/or lungs and/or isolated sound samples known to include, and associated with corresponding labels, suspect sounds (e.g., as determined by a physician or other auscultation-trained health worker) and/or the criteria model may be trained using isolated sound samples from patients known to have healthy functioning organs (e.g., heart and/or lungs) and/or known to not include a suspect sound (e.g., as determined by a physician or other auscultation-trained health worker). Based on the isolated sound samples used for training, the criteria model may be trained to identify patterns between suspect sounds that relate to frequency, timing, continuity, and/or other criteria. For example, the criteria model may determine that a first frequency bandpass should be used to evaluate whether a particular suspect sound was present in the isolated sound sample when the isolated sound sample satisfies a first timing criteria and that a second frequency bandpass should be used to evaluate whether the particular suspect sound was present in the isolated sound sample when the isolated sound sample satisfies a second timing criteria. In an example embodiment, the criteria model use sectional comparisons to evaluate whether a suspect sound or a suspect sound of a particular type was present in the isolated sound sample. For example, the criteria model may use a decision tree data structure and/or the like to evaluate whether a suspect sound or a suspect sound of a particular type was present in the isolated sound sample.

D. Exemplary Removal of Heart Sounds from Auscultation Audio Sample

In various embodiments, heart or lung sounds are removed from auscultation audio samples of an instance of data samples based on the signals of the instance of data samples for tracking the corresponding one of the patient's cardiac or respiratory cycle while the data samples were captured. For example, when the instance of data samples is being used to monitor the functioning of the patient's heart, the lung sounds may be removed from the auscultation audio samples such that the presence of suspect sounds caused by the functioning of the patient's heart may be investigated. For example, when the instance of data samples is being used to monitor the functioning of the patient's lungs, the heart sounds may be removed from the auscultation audio samples such that the presence of suspect sounds caused by the functioning of the patient's lungs may be investigated. FIG. 8 provides a flowchart illustrating various processes, procedures, operations, and/or the like for removing heart sounds from an auscultation audio sample based at least in part on a signal for tracking the patient's cardiac cycle that is part of the same instance of data samples. As should be understood, a similar process may be performed to remove lung sounds from an auscultation audio sample based at least in part on a signal for tracking the patient's respiratory cycle that is part of the same instance of data samples.

Starting at step/operation 802, the signals of the instance of data samples used to track the cardiac cycle of the patient are used to identify the heart sounds (e.g., sounds generated by the functioning of the patient's heart) in the auscultation audio sample. For example, the processing element 405, 308, 205 may use the signal(s) of the instance of data samples used to track the cardiac cycle of the patient to identify the heart sounds within the auscultation audio sample. For example, the signals of the instance of data samples used to track the cardiac cycle of the patient may comprise a pulse or other indication of when a heartbeat occurred during the capturing of the instance of data samples. Based on knowing when during the capturing of the instance of data samples a heartbeat occurred, the heart pulse rate and heartbeat waveform are detected within the auscultation audio sample. Thus, the timing of the heart beats and the amplitude of the heartbeat waveform may be determined. The timing and amplitude of the heartbeat waveform may be stored for future use.

At step/operation 804, the heart sounds are filtered and/or removed from the auscultation audio sample. In particular, the auscultation audio sample may be filtered during a time window having a defined duration (e.g., approximately 50-150 milliseconds, approximately 100 milliseconds) at the time when a heartbeat occurs. In an example embodiment, the filter may be configured to filter sounds in a particular frequency range (e.g., the 20-150 Hz range) during the time window that occurs at the time when the heartbeat occurs. For example, the processing element 405, 308, 205 may cause a timing and filtering circuit of the sound analysis circuitry 430, or other appropriate sound analysis circuit, to filter the heart sounds out of the auscultation audio sample in time windows that include the occurrence of a heartbeat during the capturing of the instance of data samples. In an example embodiment, the filtering of the heart sounds includes filtering out sounds in the particular frequency range from the auscultation audio sample, but only during the time windows that occur when the heartbeat occurs.

At step/operation 806, markers, tags, and/or the like are injected into the auscultation audio sample from which the heart sounds were removed at pulse increments. For example, the processing element 405, 308, 205 may inject markers, tags, and/or the like into the auscultation audio sample from which the heart sounds were removed at pulse increments. For example, the markers, tags, and/or the like may indicate when the heartbeat occurred and/or otherwise specify a beginning and/or end of a cardiac cycle, a portion of a cardiac cycle, and/or the like.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, the foregoing description provides the generation of complex instrument positioning maps by a server and shown to a user using graphical mapping locations in an AR view. However, it should be understood that various embodiments of the systems and methods discussed herein may be performed locally, for example, at a clinician's computing device, and/or the like.

The invention claimed is:

1. A computer-implemented method comprising:
receiving, by one or more processors, an instance of data samples, the instance of data samples comprising (a) at least two audio samples and (b) at least one of respiratory data or cardiac cycle data, the at least two audio samples comprising auscultation sounds of an individual;
generating, by the one or more processors, at least one of (a) at least two lung sound samples based at least in part on the at least two audio samples or (b) at least two heart sound samples based at least in part on the at least two audio samples by removing at least one of heart sounds or lung sounds from the at least two audio samples based at least in part on the at least one of the respiratory data or the cardiac cycle data;
identifying, by the one or more processors, a primary sound sample and at least one secondary sound sample from at least one of (a) the at least two lung sound samples or (b) the at least two heart sound samples;
at least one of (a) generating a modified secondary sound sample by changing a phase of the at least one secondary sound sample or (b) accessing a baseline sample from memory and generating a modified baseline sample by changing a phase of the baseline sample;
generating an isolated sound sample by combining the primary sound sample with at least one of (a) the modified secondary sound sample or (b) the modified baseline sample; and
determining whether the isolated sound sample includes a suspect heart or lung sound.

2. The method of claim 1, wherein the at least two audio samples were captured simultaneously.

3. The method of claim 1, wherein (a) the cardiac cycle data comprises pulse data and (b) the respiratory cycle data comprises a stretch sensor signal indicating expansion and contraction of a patient's chest due to inhalation and exhalation.

4. The method of claim 1, wherein determining whether the isolated sound sample includes the suspect heart or lung sound comprises identifying the suspect heart or lung sound in the isolated sound sample based at least in part on at least one of one or more frequency criteria, timing criteria, or consistency criteria.

5. The method of claim 4, wherein the one or more frequency criteria comprise one or more frequency bandpass filters.

6. The method of claim 1, further comprising adding the isolated sound sample to itself prior to determining whether the isolated sound sample includes the suspect heart or lung sound.

7. The method of claim 1, further comprising:
identifying the suspect heart or lung sound in the isolated sound sample; and
storing (a) an identifier of the suspect heart or lung sound and (b) at least one of the instance of data samples or the isolated sound sample.

8. The method of claim 7, wherein the suspect heart or lung sound and the at least one of the instance of data samples or the isolated sound sample are stored in association with metadata corresponding to a monitoring session in which the instance of data samples were captured for a patient.

9. The method of claim 1, wherein the determination of whether the isolated sound sample comprises the suspect heart or lung sound is performed by a machine learning-trained model.

10. The method of claim 1, wherein the modified secondary sound sample is generated by an operational amplifier.

11. The method of claim 1, wherein (a) when the modified secondary sound sample is combined with the primary sound sample, no alignment of the modified secondary sound sample and the primary sound sample is performed and (b) when the modified baseline sample is combined with the primary sound sample, an alignment of the modified baseline sample and the primary sound sample is performed.

12. The method of claim 1, wherein the suspect heart or lung sound is generated by the functioning of a respective one of a patient's heart or lungs.

13. The method of claim 1, further comprising:
responsive to determining that the isolated sound sample comprises the suspect heart or lung sound, identifying instructions to provide for capturing of an additional instance of data samples;
providing the instructions and capturing the additional instance of data samples;
generating an additional isolated sound sample by analyzing the additional instance of data samples; and
providing the additional isolated sound sample to be at least one of (a) stored in the memory or (b) graphically or audibly provided to a user.

14. The method of claim 13, wherein the instructions indicate a context that a patient should perform during the capturing of the additional instance of data samples.

15. The method of claim 14, wherein the context comprises at least one of (a) a body position, (b) a movement, (c) a breathing pattern, or (d) a word to speak.

16. The method of claim 1, further comprising, when the modified secondary sound sample is combined with the primary sound sample, storing the isolated sound sample as a baseline sample in the memory.

17. A computing apparatus comprising memory and one or more processors communicatively coupled to the memory, the one or more processors configured to:
receive an instance of data samples, the instance of data samples comprising (a) at least two audio samples and (b) at least one of respiratory data or cardiac cycle data, the at least two audio samples comprising auscultation sounds of an individual;
generate at least one of (a) at least two lung sound samples based at least in part on the at least two audio samples or (b) at least two heart sound samples based at least in part on the at least two audio samples by removing at least one of heart sounds or lung sounds from the at least two audio samples based at least in part on the at least one of the respiratory data or the cardiac cycle data;
identify a primary sound sample and at least one secondary sound sample from at least one of (a) the at least two lung sound samples or (b) the at least two heart sound samples;
at least one of (a) generate a modified secondary sound sample by changing a phase of the at least one secondary sound sample or (b) access a baseline sample from memory and generating a modified baseline sample by changing a phase of the baseline sample;
generate an isolated sound sample by combining the primary sound sample with at least one of (a) the modified secondary sound sample or (b) the modified baseline sample; and
determine whether the isolated sound sample includes a suspect heart or lung sound.

18. The computing apparatus of claim 17, wherein determining whether the isolated sound sample includes the suspect heart or lung sound comprises identifying the suspect heart or lung sound in the isolated sound sample based at least in part on at least one of one or more frequency criteria, timing criteria, or consistency criteria.

19. The computing apparatus of claim 18, wherein the one or more frequency criteria comprise one or more frequency bandpass filters.

20. One or more non-transitory computer-readable storage media including instructions that, when executed by one or more processors, cause the one or more processors to:
receive an instance of data samples, the instance of data samples comprising (a) at least two audio samples and (b) at least one of respiratory data or cardiac cycle data, the at least two audio samples comprising auscultation sounds of an individual;
generate at least one of (a) at least two lung sound samples based at least in part on the at least two audio samples or (b) at least two heart sound samples based at least in part on the at least two audio samples by removing at least one of heart sounds or lung sounds from the at least two audio samples based at least in part on the at least one of the respiratory data or the cardiac cycle data;
identify a primary sound sample and at least one secondary sound sample from at least one of (a) the at least two lung sound samples or (b) the at least two heart sound samples;
at least one of (a) generate a modified secondary sound sample by changing a phase of the at least one secondary sound sample or (b) access a baseline sample from memory and generating a modified baseline sample by changing a phase of the baseline sample;
generate an isolated sound sample by combining the primary sound sample with at least one of (a) the modified secondary sound sample or (b) the modified baseline sample; and
determine whether the isolated sound sample includes a suspect heart or lung sound.

\* \* \* \* \*

UNITED STATES PATENT AND TRADEMARK OFFICE
CERTIFICATE OF CORRECTION

| | | |
|---|---|---|
| PATENT NO. | : 11,751,774 B2 | Page 1 of 1 |
| APPLICATION NO. | : 17/096035 | |
| DATED | : September 12, 2023 | |
| INVENTOR(S) | : Jon Kevin Muse et al. | |

It is certified that error appears in the above-identified patent and that said Letters Patent is hereby corrected as shown below:

On the Title Page

Please insert item (60), Related U.S. Application Data, as follows:
-- Provisional application no. 63/057,543, filed on July 28, 2020. --

Signed and Sealed this
Seventeenth Day of September, 2024

Katherine Kelly Vidal
*Director of the United States Patent and Trademark Office*